US012383320B2

(12) United States Patent
Reed

(10) Patent No.: US 12,383,320 B2
(45) **Date of Patent: *Aug. 12, 2025**

(54) SYSTEMS, METHODS, AND PROGRAM PRODUCTS FOR A DISTRIBUTED DIGITAL ASSET NETWORK WITH RAPID TRANSACTION SETTLEMENTS

(71) Applicant: AI COIN INC., Hoboken, NJ (US)

(72) Inventor: Stephen Lester Reed, Austin, TX (US)

(73) Assignee: AI COIN INC., Hoboken, NJ (US)

(*) Notice: Subject to any disclaimer, the term of this patent is extended or adjusted under 35 U.S.C. 154(b) by 360 days.

This patent is subject to a terminal disclaimer.

(21) Appl. No.: 17/878,209

(22) Filed: Aug. 1, 2022

(65) Prior Publication Data

US 2022/0370108 A1 Nov. 24, 2022

Related U.S. Application Data

(63) Continuation of application No. 16/748,158, filed on Jan. 21, 2020, now Pat. No. 11,403,605, which is a continuation of application No. 15/045,148, filed on Feb. 16, 2016, now Pat. No. 10,579,974.

(60) Provisional application No. 62/116,852, filed on Feb. 16, 2015.

(51) Int. Cl.

| | |
|---|---|
| ***G06Q 20/10*** | (2012.01) |
| ***A61B 17/84*** | (2006.01) |
| ***A61B 17/86*** | (2006.01) |
| ***A61B 17/88*** | (2006.01) |
| ***G06Q 20/06*** | (2012.01) |
| ***G06Q 20/36*** | (2012.01) |
| ***G06Q 20/38*** | (2012.01) |
| *A61B 17/90* | (2006.01) |

(52) U.S. Cl.

CPC .......... *A61B 17/8625* (2013.01); *A61B 17/84* (2013.01); *A61B 17/8875* (2013.01); *G06Q 20/065* (2013.01); *G06Q 20/105* (2013.01); *G06Q 20/3678* (2013.01); *G06Q 20/389* (2013.01); *A61B 17/90* (2021.08)

(58) Field of Classification Search

None

See application file for complete search history.

(56) References Cited

U.S. PATENT DOCUMENTS

| | | | | |
|---|---|---|---|---|
| 9,800,517 | B1 * | 10/2017 | Anderson | H04L 47/70 |
| 9,875,510 | B1 * | 1/2018 | Kasper | G06Q 40/12 |
| 9,898,587 | B2 * | 2/2018 | Hahn | H04L 9/3263 |
| 9,898,782 | B1 * | 2/2018 | Winklevoss | G06Q 40/04 |
| 2013/0325701 | A1 * | 12/2013 | Schwartz | G06Q 40/00 705/39 |

(Continued)

OTHER PUBLICATIONS

Daniel Cawrey, "What Are Bitcoin Nodes and Why Do We Need Them?", May 9, 2014, CoinDesk (wwwcoindesk.com/bitcoin-nodes-need) pp. 1 through 9 (Year: 2014).*

(Continued)

*Primary Examiner* — Benjamin S Brindley
(74) *Attorney, Agent, or Firm* — Amster, Rothstein & Ebenstein LLP

(57) ABSTRACT

Systems, methods, and program products for providing and administering a digital asset network of cooperative nodes with rapid transaction settlements are disclosed.

13 Claims, 20 Drawing Sheets

(56) References Cited

U.S. PATENT DOCUMENTS

| | | | | |
|---|---|---|---|---|
| 2014/0164251 A1* | 6/2014 | Loh | G06Q 20/065 | 705/67 |
| 2014/0359289 A1* | 12/2014 | Camenisch | H04L 9/30 | 713/168 |
| 2015/0120569 A1* | 4/2015 | Belshe | G06Q 20/3829 | 705/71 |
| 2015/0170112 A1* | 6/2015 | DeCastro | G06Q 20/367 | 705/39 |
| 2015/0193744 A1* | 7/2015 | Adleman | H04L 9/3247 | 705/69 |
| 2015/0269541 A1* | 9/2015 | MacGregor | H04L 9/321 | 705/39 |
| 2015/0310424 A1* | 10/2015 | Myers | G06Q 20/401 | 705/69 |
| 2015/0363783 A1* | 12/2015 | Ronca | G06Q 20/382 | 705/71 |

OTHER PUBLICATIONS

Satoshi Nakamoto, "Bitcoin: A Peer-to-Peer Electronic Cash System" (2009), https://bitcoin.org/bitcoin.pdf.

"Data Propagation", BitcoinStats, available at http://bitcoinstats.com/network/propagation/, last visited May 11, 2016.

Visa, "VisaNet The technology behind Visa" (2013), http://usa.visa.com/download/corporate/_media/visanet-technology/visa-net-booklet.pdf.

SWIFT, "SWIFT Messaging Services, Distributed Architecture Phase 1, White Paper, Version 1.5" (Dec. 2009), http://www.swift.com/solutions/industry_initiatives/image_doc/DA_Phase_1_white_paper_200912_1_5.pdf.

"Payment Card Industry (PCI) Data Security Standard Version 3.0", PCI Security Standards Council (Nov. 2013), https://www.pcisecuritystandards.org/documents/PCI_DSS_v3.pdf.

Jameson Lopp, "Bitcoin Nodes: How Many is Enough? Should we be worried about the declining number of nodes?" (Jun. 7, 2014), http://coinchomp.com/2014/03/19/bitcoin-nodes-many-enough/.

Daniel Cawrey, "What Are Bitcoin Nodes and Why Do We Need Them?", CoinDesk (May 9, 2014), http://www.coindesk.com/bitcoin-nodes-need/.

"Global Bitcoin Nodes Distribution", BitNodes, available at https://getaddr.bitnodes.io/, last visited Mar. 30, 2016.

Tim Swanson, "Learning from Bitcoin's past to improve its future" (Apr. 27, 2014), http://www.ofnumbers.com/wp-content/uploads/2014/04/Learning-from-Bitcoins-past.pdf.

Bitrick, "Satoshi Client Operation: Overview", Bitcoin Forum (Sept. 5, 2011), https://bitcointalk.org/index.php?topic=41718.msg507953#msg507953.

Krzysztof Okupski, "Bitcoin Developer Reference Working Paper" (Dec. 17, 2015), http://enetium.com/resources/Bitcoin.pdf.

Andrew Miller et al., "Anonymous Byzantine Consensus from Moderately-Hard Puzzles: A Model for Bitcoin" (Apr. 27, 2014), https://socrates1024.s3.amazonaws.com/consensus.pdf.

Ben Laurie, "Decentralised Currencies Are Probably Impossible but Let's at Least Make Them Efficient" (Jul. 5, 2011), http://www.links.org/files/decentralised-currencies.pdf.

Sunny King, "Primecoin: Cryptocurrency with Prime No. Proof-of-Work" (Jul. 7, 2013), http://primecoin.org/static/primecoin-paper.pdf.

Quantummechanic, "Proof of stake instead of proof of work", Bitcoin Forum (Jul. 10, 2011), https://bitcointalk.org/index.php?topic=27787.msg349645#msg349645.

Sunny King et al., "PPCoin: Peer-to-Peer Crypto-Currency with Proof-of-Stake" (Aug. 19, 2012), http://peercoin.net/assets/paper/peercoin-paper.pdf.

"Crypto-Currency Market Capitalizations", CoinMarketCap, available at https://coinmarketcap.com/, last accessed Mar. 30, 2016.

Vitalik Buterin, "What Proof of Stake Is and Why It Matters", Bitcoin Magazine (Aug. 26, 2013), http://bitcoinmagazine.com/6528/.

Nicolas Houy, "It Will Cost You Nothing to 'Kill' a Proof-of-Stake Crypto-Currency", Social Science Research Network (Feb. 11, 2014), http://papers.ssrn.com/sol3/papers.cfm?abstract_id=2393940.

Lacksfish, "What stops me from POS minting several different chains at once?", Peercoin Talk forum (Jan. 9, 2014), available at http://www.peercointalk.org/index.php?topic=1956.0.

Stakehunter, "Proof of Stake Coin List", Bitcoin Forum (Feb. 10, 2014), available at https://bitcointalk.org/index.php?topic=458726.0, last visited May 13, 2016.

Nick Szabo, "Distributing Authorities and Verifying Their Claims" (1997), http://szabo.best.vwh.net/authorities.html.

Nick Szabo, "The God Protocols" (1999), http://szabo.best.vwh.net/msc.html.

Nick Szabo, "Confidential Auditing" (1998), http://szabo.best.vwh.net/confidential.html.

Andrew Miller et al., "Authenticated Data Structures, Generically" (2014), POPL 2014: 41st ACM SIGPLAN-SIGACT Symposium on Principles of Programming Languages, http://www.cs.umd.edu/~mwh/papers/miller14gpads.html.

Petros Maniatis et al., "Secure History Preservation through Timeline Entanglement", Proceedings of the 11th USENIX Security Symposium (2002), http://www.usenix.org/events/sec02/full_papers/maniatis/maniatis.pdf.

Nick Szabo, "Trusted Third Parties Are Security Holes", Satoshi Nakamoto Institute (2005, originally published 2001), http://nakamotoinstitute.org/literature/18/html/.

Andreas Haeberlen et al., "PeerReview: Practical Accountability for Distributed Systems" (2007), http://infosec.pku.edu.cn/~p2p/slides/%5BSOSP07%5D PeerReview—Practical Accountability for Distributed Systems.pdf.

Beverly Yang et al., "Designing a Super-Peer Network" (2003), http://ilpubs.stanford.edu:8090/594/1/2003-33.pdf.

G. Keith Cambron, Global Networks, Engineering, Operations, and Design, Wiley, 2013, pp. 125-148.

Byung-Gon Chun, "Attested Append-Only Memory: Making Adversaries Stick to their Word" (2007), http://iris.csail.mit.edu/irisbib/papers/aaom:sosp21/paper.pdf.

Miguel Correia et al., "Byzantine consensus in asynchronous message-passing systems: a survey", Int. J. Critical Computer-Based Systems, Vo. 2, No. 2 (2011), http://citeseerx.ist.psu.edu/viewdoc/download?doi=10.1.1.301.5623&rep=rep1&type=pdf.

Jan Sacha et al., "Discovery of Stable Peers in a Self-Organising Peer-to-Peer Gradient Topology" (2006), http://www.researchgate.net/publication/220973572_Discovery_of_Stable_Peers_in_a_Self-organising_Peer-to-Peer_Gradient_Topology/file/79e4150bdcabb3e279.pdf.

Oscar Williams-Grut, "Blockchain startup itBit is opening a London office—here's what its CEM told us about its plans", Business Insider (Feb. 16, 2016), available at http://www.businessinsider.com/itbit-ceo-chad-cascarilla-blockchain-london-2016-2?r=UK&IR=T, last visited May 20, 2016.

Natalie Rodriguez, "4 Ways Bitcoin's Tech May Soon Change Lawyers' Lives", Law 360 (Feb. 10, 2016), available at http://www.law360.com/ip/articles/756907, last visited Jul. 6, 2016.

* cited by examiner

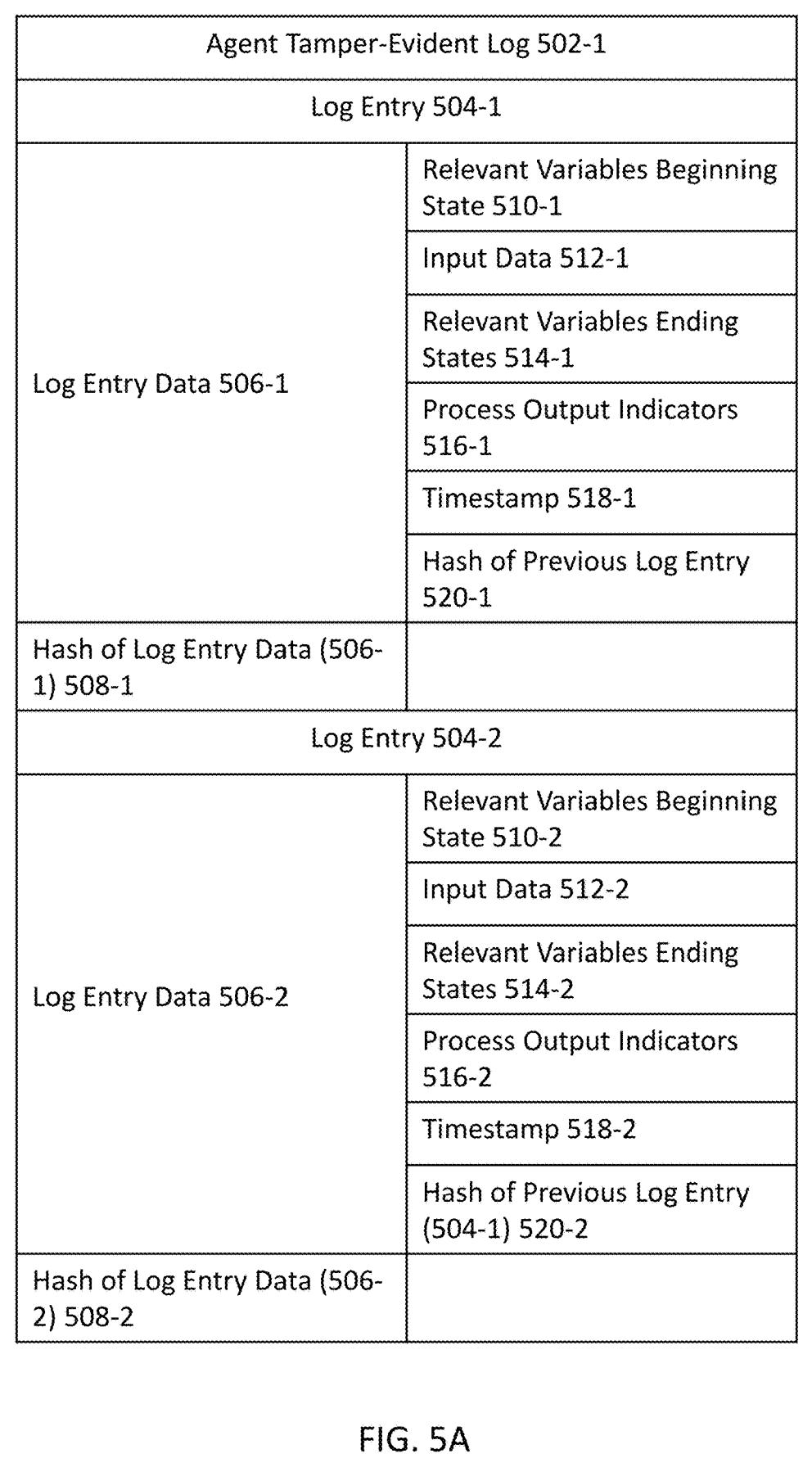

| Agent Tamper-Evident Log 502-1 | |
|---|---|
| Log Entry 504-1 | |
| Log Entry Data 506-1 | Relevant Variables Beginning State 510-1 |
| | Input Data 512-1 |
| | Relevant Variables Ending States 514-1 |
| | Process Output Indicators 516-1 |
| | Timestamp 518-1 |
| | Hash of Previous Log Entry 520-1 |
| Hash of Log Entry Data (506-1) 508-1 | |
| Log Entry 504-2 | |
| Log Entry Data 506-2 | Relevant Variables Beginning State 510-2 |
| | Input Data 512-2 |
| | Relevant Variables Ending States 514-2 |
| | Process Output Indicators 516-2 |
| | Timestamp 518-2 |
| | Hash of Previous Log Entry (504-1) 520-2 |
| Hash of Log Entry Data (506-2) 508-2 | |

FIG. 5A

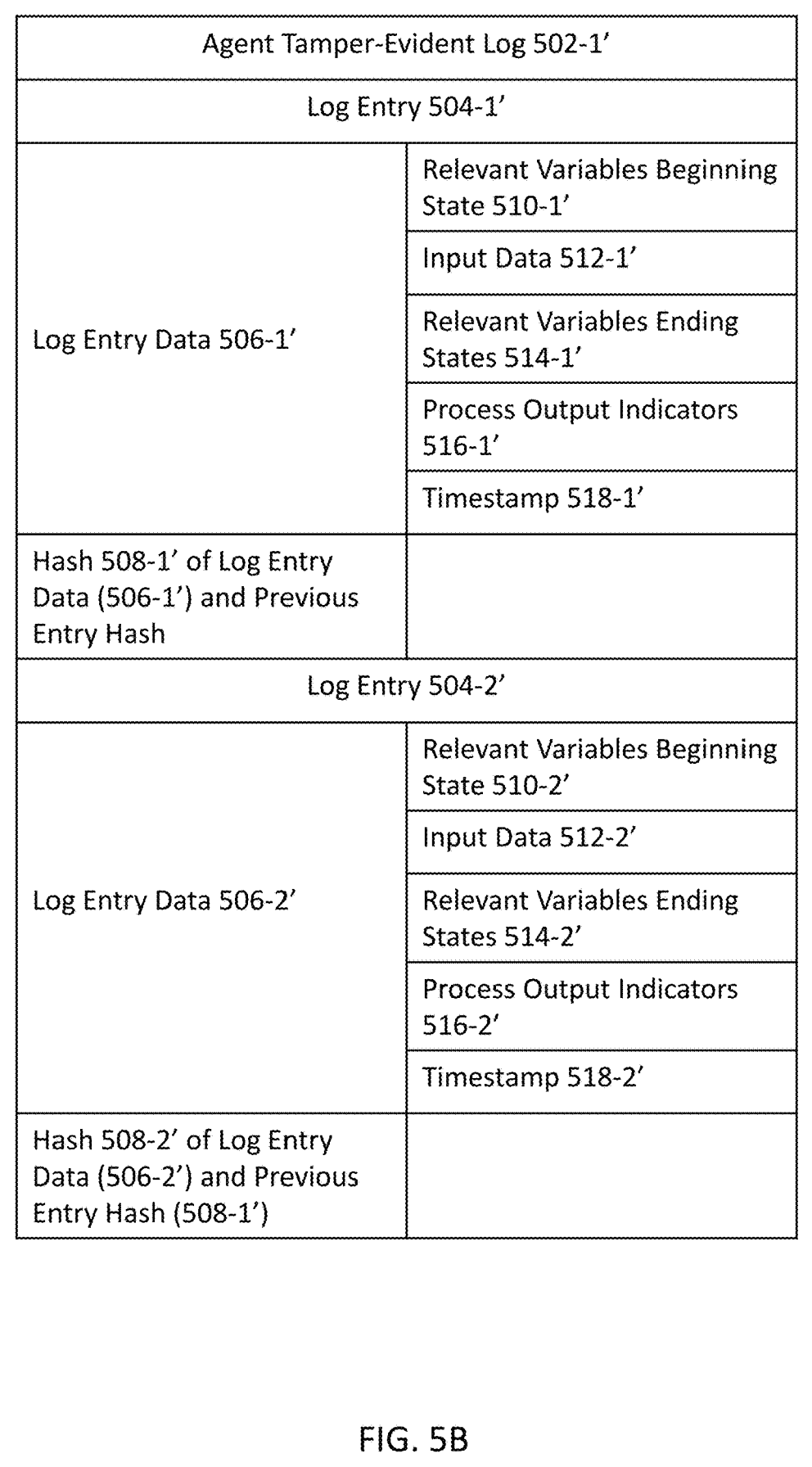

| Agent Tamper-Evident Log 502-1′ | |
|---|---|
| Log Entry 504-1′ | |
| Log Entry Data 506-1′ | Relevant Variables Beginning State 510-1′ |
| | Input Data 512-1′ |
| | Relevant Variables Ending States 514-1′ |
| | Process Output Indicators 516-1′ |
| | Timestamp 518-1′ |
| Hash 508-1′ of Log Entry Data (506-1′) and Previous Entry Hash | |
| Log Entry 504-2′ | |
| Log Entry Data 506-2′ | Relevant Variables Beginning State 510-2′ |
| | Input Data 512-2′ |
| | Relevant Variables Ending States 514-2′ |
| | Process Output Indicators 516-2′ |
| | Timestamp 518-2′ |
| Hash 508-2′ of Log Entry Data (506-2′) and Previous Entry Hash (508-1′) | |

FIG. 5B

<table>
<tr><td colspan="2">Agent Tamper-Evident Log 502-1"</td></tr>
<tr><td colspan="2">Log Entry 504-3</td></tr>
<tr><td rowspan="5">Log Entry Data 506-3</td><td>Relevant Variables Beginning State 506-3</td></tr>
<tr><td>Input Data 508-3</td></tr>
<tr><td>Relevant Variables Ending States 510-3</td></tr>
<tr><td>Process Output Indicators 512-3</td></tr>
<tr><td>Timestamp 514-3</td></tr>
<tr><td>Hash 508-3 of Log Entry Data (506-3) and Previous Entry Hash</td><td></td></tr>
<tr><td colspan="2">Log Audit Entry 504-4</td></tr>
<tr><td rowspan="3">Log Audit Entry Data 506-4</td><td>Auditor (Remote) Timestamp 520-1</td></tr>
<tr><td>Auditor Digital Signature 522-1</td></tr>
<tr><td>(Local) Timestamp 518-4</td></tr>
<tr><td>Hash 508-4 of Log Audit Entry Data (506-4) and Previous Entry Hash (508-3)</td><td></td></tr>
</table>

FIG. 5C

S732: Receiving, at a non-minting software agent (e.g., running on one of a plurality of super peer computing nodes), transaction parameters for a pending digital asset transaction.

S734: Recording, by the non-minting software agent, the transaction parameters in a respective tamper-evident log stored in respective non-transitory computer-readable memory.

S736: Receiving, at the non-minting software agent from a minting software agent, an electronic indication of transaction validity for the pending digital asset transaction.

S738: Recording, by the non-minting software agent, the electronic indication of transaction validity for the pending digital asset transaction in the respective tamper-evident log.

S740: Relaying, from the non-minting software agent to one or more gateway nodes, the electronic indication of transaction validity for the pending digital asset transaction to be delivered at least to respective user devices associated with the pending digital asset transaction.

S742: Accessing, by the non-minting software agent, a second tamper-evident log of at least one software agent of another super peer computing node.

S744: Auditing, by the non-minting software agent, the second tamper-evident log. [See FIG. 7D]

S746: Computing, by the non-minting software agent, a respective independent instance of a first electronic ledger portion of a distributed electronic public ledger.

S748: Receiving, at the non-minting software agent from the minting software agent, data comprising at least a first master electronic ledger portion of the distributed electronic public ledger.

S750: Comparing, by the non-minting software agent, the respective independent instance of the first electronic ledger portion with the received data comprising at least the first master electronic ledger portion.

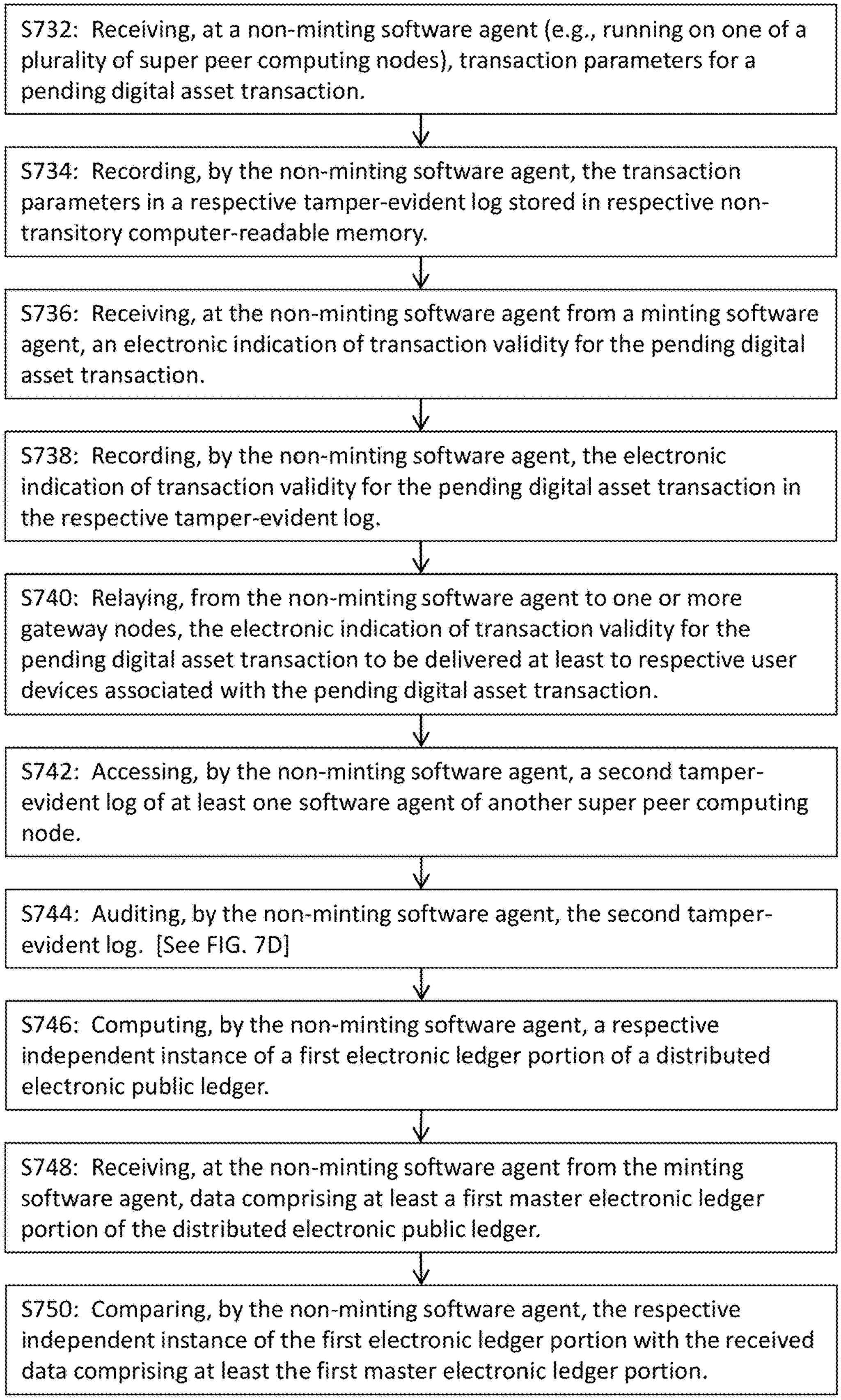

FIG. 7C

| | Super Peer 802-1 | Super Peer 802-2 | Super Peer 802-3 |
|---|---|---|---|
| $T_1$ | Minting Agent 804-1 | Non-Minting Agent 806-2 | Non-Minting Agent 806-3 |
| $T_2$ | Non-Minting Agent 806-1 | Minting Agent 804-2 | Non-Minting Agent 806-3 |
| $T_3$ | Non-Minting Agent 806-1 | Non-Minting Agent 806-2 | Minting Agent 804-3 |

FIG. 8

SYSTEMS, METHODS, AND PROGRAM PRODUCTS FOR A DISTRIBUTED DIGITAL ASSET NETWORK WITH RAPID TRANSACTION SETTLEMENTS

CROSS-REFERENCE TO RELATED APPLICATIONS

This application claims the benefit of and priority to U.S. patent application Ser. No. 16/748,158, filed Jan. 21, 2020 and entitled SYSTEMS, METHODS, AND PROGRAM PRODUCTS FOR A DISTRIBUTED DIGITAL ASSET NETWORK WITH RAPID TRANSACTION SETTLEMENTS, which in turn claims the benefit of and priority to U.S. patent application Ser. No. 15/045,148, filed Feb. 16, 2016 and entitled SYSTEMS, METHODS, AND PROGRAM PRODUCTS FOR A DISTRIBUTED DIGITAL ASSET NETWORK WITH RAPID TRANSACTION SETTLEMENTS, which in turn claims the benefit of and priority to U.S. Provisional Patent Application Ser. No. 62/116,853, filed Feb. 16, 2015, and the contents of these applications are incorporated herein by reference in their entirety.

FIELD OF THE INVENTION

The present invention generally relates to systems, methods, and program products for providing and administering a digital asset network with rapid transaction settlements.

BACKGROUND OF THE INVENTION

Prior art digital assets, such as Bitcoin, utilize competition among nodes in the digital asset network in order to provide confirmation of transactions. Nodes known as miners compete to solve a computationally intensive mathematical puzzle in order to confirm pending digital asset transactions. Confirming transactions can also entail the minting of new digital assets. Upon confirmation of the transactions, a distributed public ledger is updated. The Bitcoin ledger is known as the blockchain. Successive blocks or portions that are appended to the blockchain ledger contain details of the confirmed transactions. Mining computers thus add a new block to the blockchain when they solve the computationally intensive puzzle. The Bitcoin governing protocol increases the difficulty of the mathematical puzzle based upon the network processing power in order to govern the mining frequency. The resulting frequency is mining of new Bitcoin blocks approximately every ten minutes, although the exact mining cycle varies since there is no guarantee of its frequency.

The mathematical puzzle is the heart of the Bitcoin proof of work system. The successful miner that solved the puzzle broadcasts the solution to other nodes in the network, which can easily confirm the solution, proving the work of the successful miner. The puzzle is difficult to solve but easy to verify. The computers in the network verify the work of the successful miner so that there is no need to trust that the successful miner indeed solved the puzzle correctly.

The mining computers in the Bitcoin system race to solve the puzzle. Bitcoin mining nodes thus participate in a competitive proof of work system. The result is ever-increasing resource consumption by the miner computers. Mining operations previously performed on average desktop computers are now being performed by consortiums of specifically designed mining computing hardware. Because the computing processing requirements and accompanying electricity consumption have become so great, what started as a distributed mining system has become centralized in a few consortiums of powerful mining computer hardware. The massive consumption of electricity required to mine bitcoins is exacerbated by the competition among miners. Since there is only one successful miner in each confirmation cycle, the resources expended by the non-successful mining computers are wasted.

Alternative digital currencies have been proposed to reduce resource consumption. However, some alternatives, such as PeerCoin, rely upon proof of stake. There is no race to solve a computationally intense puzzle, as the amount of the digital asset owned is used to select the miner. However, this type of system encourages hoarding of digital assets, which undermines a robust digital asset ecosystem such as one that could be used as a payment network. Also, because competition still exists to confirm transactions, there can be instabilities and risks of double spending the digital asset and/or orphan transactions that do not get confirmed. Bitcoin suffers some of these same problems. Transacting participants are advised to wait about six confirmation cycles (mining cycles) to have assurance that their transaction was indeed confirmed by a majority of the network and not just confirmed in an orphan block. An orphan block is a block that is not part of the main blockchain. It can be caused by the competitive mining process, where multiple miners solve the puzzle and thus confirm certain transactions at a similar time. Each successful miner will propagate its latest block, which other miners will build upon in solving the next block. However, only the blockchain that is recognized by the majority of the network is the valid blockchain. Accordingly, orphan block chains may grow for a number of mining cycles until the valid blockchain eventually takes over. Thus there is a need to wait for much longer than the mining confirmation cycle in order to have assurance that the digital asset network recognizes a transaction as confirmed. Reducing the time period of a mining cycle does not necessarily solve the problem. Because blocks are added to the blockchain faster, off-shoots of the main blockchain simply grow faster such that the same number of confirmation cycles no longer gives assurance that a transaction is part of the main blockchain. Accordingly, a higher number of confirmation cycles must be waited to have assurance that a transaction is recognized by the majority of the network.

A major feature of many digital assets including Bitcoin is their decentralization. There is no central control but rather the processing of the network provides authority to confirm transactions. This is viewed as a beneficial alternative to payment networks and/or currency systems with centralized control, which can have weakness due to a single point of attack and/or can be controlled by a select minority (e.g., a government or a corporation), which may exercise unrestricted influence. For example, a corporation running a centralized payment network may charge large transaction processing fees, or a government may adjust the amount of a currency in circulation or otherwise alter the value. Moreover, a government-provided currency may have territorial restrictions.

There is a need for a digital asset system that provides near-instant or rapid confirmation without having to wait to ensure that confirmed transactions are indeed recognized by a majority of the digital asset network. There is a further desire to provide such a system without requiring intense resource consumption. It remains desirable to provide a trustless digital asset system, where nodes in the network need not trust the work of other nodes, such as mining nodes.

Such a trustless system can increase security of the digital asset network. It is also desirable to eliminate risks of double spending the asset.

SUMMARY OF THE INVENTION

Systems, methods, and program products for providing and administering a digital asset network with rapid transaction settlements are disclosed.

In embodiments, a digital asset system is disclosed comprising a plurality of super peer computing nodes operating in a cooperative computing architecture to facilitate provision of a digital asset network using proof of work, each node comprising respective one or more processors and respective non-transitory computer-readable memory and configured to run on its respective one or more processors one or more software agents to administer the digital asset network. The digital asset system further comprises an administrative super peer computing node running a configuration software agent that schedules computing roles for the plurality of super peer computing nodes, wherein the configuration software agent schedules for a first period of time a first one of the plurality of super peer computing nodes to run a first minting software agent configured to perform respective minting agent operations comprising: receiving transaction parameters for a pending digital asset transaction involving two or more digital asset addresses, the transaction parameters comprising one or more digital asset transaction inputs each comprising an input amount and a respective digital signature and associated with a sending digital asset address, and the transaction parameters further comprising at least one digital asset transaction output associated with a receiving digital asset address; recording the transaction parameters in a first tamper-evident log stored in first non-transitory computer-readable memory, wherein each entry in the first tamper-evident log comprises (1) respective first log entry data comprising at least the transaction data and a first timestamp and (2) a respective first hash of the respective first log entry data; verifying the pending digital asset transaction at least by evaluating the respective digital signature associated with each digital asset transaction input to confirm the digital asset transaction input is an authorized input and previously unspent and by confirming that the sum of the authorized inputs equals or exceeds the digital asset transaction output; recording in the first tamper-evident log a first electronic indication of the transaction validity for the verified pending digital asset transaction; transmitting, to one or more others of the plurality of super peer computing nodes, a second electronic indication of the transaction validity for the verified pending digital asset transaction, the second electronic indication of the transaction validity providing a transaction settlement indication without waiting for a consensus, by nodes of the digital asset network, of accuracy of a distributed electronic public ledger; appending, according to a periodic schedule, to a first instance of a distributed electronic public ledger stored in the first non-transitory computer-readable memory a first electronic ledger portion comprising transaction details for the verified pending digital asset transaction along with respective transaction details for any other verified pending digital asset transactions not yet included in the first instance of the distributed electronic public ledger; transmitting data comprising at least the first electronic ledger portion to the others of the plurality of super peer computing nodes; and auditing a respective tamper-evident log of at least one software agent of one of the others of the plurality of super peer computing nodes.

Further, the configuration software agent schedules for the first period of time the others of the plurality of super peer computing nodes to run respective non-minting software agents wherein at least some of the non-minting software agents are configured to perform the steps of: receiving the transaction parameters for the pending digital asset transaction; recording the transaction parameters in a respective second tamper-evident log stored in respective non-transitory computer-readable memory; receiving, from the first minting software agent, the second electronic indication of the transaction validity for the verified pending digital asset transaction; recording the second electronic indication of the transaction validity for the verified pending digital asset transaction in the respective second tamper-evident log; accessing respective third tamper-evident logs of at least some of the plurality of super peer computing nodes to verify entries in the respective second tamper-evident log; relaying to one or more gateway nodes the second electronic indication of the transaction validity for the verified pending digital asset transaction to be delivered at least to respective user devices associated with the two or more digital asset addresses; computing a respective independent instance of the first electronic ledger portion; receiving, from the first minting software agent, data comprising at least the first electronic ledger portion; and comparing the respective independent instance of the first electronic ledger portion with the received data comprising at least the first electronic ledger portion.

Further, the configuration software agent schedules for a second period of time a second one of the plurality of super peer computing nodes to run a second minting software agent to perform respective minting agent operations.

In embodiments, the configuration software agent schedules computing roles for the plurality of super peer computing nodes according to a predefined schedule stored in respective non-transitory computer-readable memory operatively connected to the administrative super peer computing node and accessible by the configuration software agent.

In embodiments, the predefined schedule may identify for each of a plurality of periods of time (e.g., comprising a daily schedule) one minting agent to be run on a respective one of the plurality of super peer computing nodes according to times when trading markets are active in a respective geographic location of the respective one of the plurality of super peer computing nodes.

In embodiments, the configuration software agent schedules computing roles for the plurality of super peer computing nodes based at least in part upon any of respective available processing power of at least one of the plurality of super peer computing nodes, respective available transmission bandwidth of at least one of the plurality of super peer computing nodes, respective ownership or control of at least one of the plurality of super peer computing nodes, or geographic location of at least one of the plurality of super peer computing nodes.

In embodiments, the first electronic ledger portion is appended to the first instance of the distributed electronic public ledger comprises creation of a predefined amount of digital assets. In embodiments, the predefined amount may be changed over time, e.g., according to a schedule or by reprogramming.

In embodiments, the periodic schedule comprises a predefined frequency with which to append new electronic ledger portions to the first instance of the distributed electronic public ledger.

In embodiments, the predefined frequency may be 30 seconds, 1 minute, 10 minutes, 1 hour, 1 day, to name a few.

In embodiments, the periodic schedule comprises one or more predefined times at which to append new electronic ledger portions to the first instance of the distributed electronic public ledger.

In embodiments, the one or more predefined times may correspond to a market opening time and/or a market closing time. In embodiments, the predefined time may be any of 12 AM E.T., 9 AM E.T., and/or 5 PM E.T., to name a few.

In embodiments, the at least some of the non-minting software agents are further configured to perform the steps of: auditing a third tamper-evident log of a third one of the others of the plurality of super peer computing nodes running a non-minting software agent; accessing a third tamper-evident log of the third one of the others of the plurality of super peer computing nodes; comparing respective log entries of the third tamper-evident log with log entries of the respective second tamper-evident log; generating an audit digital signature by computing a second hash of a last previous log entry in the third tamper-evident log and encrypting the second hash using a respective private key of an asymmetric key pair; recording in the respective second tamper-evident log an indication of the audit of the third tamper-evident log; and providing the audit digital signature to the third one of the others of the plurality of super peer computing nodes to be appended to the third tamper-evident log, wherein appending the audit digital signature entangles the third tamper-evident log with the respective software agent that provided the audit digital signature, eliminating the ability to alter past entries in the third tamper-evident log without discrepancy with the respective second tamper-evident log.

In embodiments, computing by each of the at least some of the non-minting software agents, the respective independent instance of the first electronic ledger portion comprises: accessing transaction parameters for a plurality of digital asset transactions from the respective second tamper-evident log of the respective non-minting software agent; determining a subset of the plurality of digital asset transactions that are unverified pending digital asset transactions for which respective indications of respective transaction validity have not been received from the first minting software agent; computing the respective independent instance of the first electronic ledger portion according to a programmed minting process.

In embodiments, during the second period of time the configuration software agent schedules the first one of the plurality of super peer computing nodes to run a respective non-minting software agent.

In embodiments, the digital asset system further comprises archiving nodes each comprising one or more respective processors and respective non-transitory computer-readable memory and configured perform the steps of: storing in the respective non-transitory computer-readable memory a respective instance of the distributed electronic public ledger; receiving data comprising at least the first electronic ledger portion; appending the first electronic ledger portion to the respective instance of the distributed electronic public ledger to generate a respective updated instance of the distributed electronic public ledger; and storing the respective updated instance of the distributed electronic public ledger.

In embodiments, a digital asset system is disclosed. The digital asset system comprises a plurality of super peer computing nodes operating in a cooperative computing architecture to facilitate provision of a digital asset network using proof of work, each node comprising respective one or more processors and respective non-transitory computer-readable memory and configured to run on its respective one or more processors one or more software agents to administer the digital asset network.

The digital asset system may further comprise an administrative super peer computing node running a configuration software agent that schedules computing roles for the plurality of super peer computing nodes.

A first one of the plurality of super peer computing nodes may run a first minting software agent during a first period of time according to scheduling instructions received from the configuration software agent, wherein the first minting software agent may be configured to perform the steps of: receiving transaction parameters for a pending digital asset transaction involving two or more digital asset addresses, the transaction parameters comprising one or more digital asset transaction inputs each comprising an input amount, a respective digital signature, and associated with a sending digital asset address, and the transaction parameters further comprising at least one digital asset transaction output associated with a receiving digital asset address; recording the transaction parameters in a first tamper-evident log stored in first non-transitory computer-readable memory, wherein each entry in the first tamper-evident log comprises a respective first hash of respective first log entry data comprising at least the transaction data, a first timestamp, and a hash of the respective previous log entry, which first hash is digitally signed using a first private key of an asymmetric key pair associated with the first minting software agent; verifying the pending digital asset transaction at least by evaluating the respective digital signature associated with each digital asset transaction input to confirm the digital asset transaction input is an authorized input and previously unspent and by confirming that the sum of the authorized inputs equals or exceeds the digital asset transaction output; recording in the first tamper-evident log a first electronic indication of the transaction validity for the verified pending digital asset transaction; transmitting, to one or more others of the plurality of super peer computing nodes, a second electronic indication of the transaction validity for the verified pending digital asset transaction, the second electronic indication of the transaction validity providing a transaction settlement indication without waiting for updates to a distributed electronic public ledger; appending, according to a periodic schedule, to a first instance of a distributed electronic public ledger stored in the first non-transitory computer-readable memory a first electronic ledger portion comprising transaction details for the verified pending digital asset transaction along with respective transaction details for any other verified pending digital asset transactions not yet included in the first instance of the distributed electronic public ledger; transmitting data comprising at least the first electronic ledger portion to the others of the plurality of super peer computing nodes; and accessing respective tamper-evident logs of at least one of the others of the plurality of super peer computing nodes, used to verify entries in the first tamper-evident log.

The system may further receive, from the configuration software agent, instructions to cease running the first minting software agent during a second period of time and to run a non-minting software agent during the second period of time configured to perform the steps of: receiving second transaction parameters for a second pending digital asset transaction; recording the second transaction parameters in a second tamper-evident log stored in respective non-transitory computer-readable memory; receiving, from a second one of the plurality of super peer computing nodes running a second minting software agent during the second period of time, an electronic indication of transaction validity associated with the second pending digital asset transaction; recording the electronic indication of transaction validity for the second pending digital asset transaction in the second tamper-evident log; accessing tamper-evident logs of at least some of the plurality of super peer computing nodes used to verify entries in the second tamper-evident log; relaying to one or more gateway nodes the electronic indication of transaction validity for the second pending digital asset transaction to be delivered at least to respective user devices associated with the second pending digital asset transaction; computing a respective independent instance of a second electronic ledger portion; receiving from the second one of the plurality of super peer computing nodes data comprising at least a minting second electronic ledger portion; and comparing the respective independent instance of the second electronic ledger portion with the received data comprising at least the minting second electronic ledger portion.

In embodiments, the configuration software agent may schedule computing roles for the plurality of super peer computing nodes according to a predefined schedule stored in respective non-transitory computer-readable memory operatively connected to the administrative super peer computing node and accessible by the configuration software agent.

In embodiments, the configuration software agent may schedule computing roles for the plurality of super peer computing nodes based at least in part upon any of respective available processing power of at least one of the plurality of super peer computing nodes, respective available transmission bandwidth of at least one of the plurality of super peer computing nodes, respective ownership or control of at least one of the plurality of super peer computing nodes, or geographic location of at least one of the plurality of super peer computing nodes.

In embodiments, the first electronic ledger portion may be appended to the first instance of the distributed electronic public ledger comprises creation of a predefined amount of digital assets.

In embodiments, the periodic schedule may comprise a predefined frequency with which to append new electronic ledger portions to the first instance of the distributed electronic public ledger.

In embodiments, the periodic schedule may comprise one or more predefined times at which to append new electronic ledger portions to the first instance of the distributed electronic public ledger.

BRIEF DESCRIPTION OF THE DRAWINGS

Exemplary embodiments of the present invention will be described with references to the accompanying figures, wherein:

FIGS. 5A-C are schematic diagrams of exemplary tamper-evident logs in accordance with exemplary embodiments of the present invention;

FIG. 7C is a flow chart of exemplary non-minting operations of a super peer computing node in accordance with exemplary embodiments of the present invention;

FIG. 8 is a schematic diagram of minting role scheduling in accordance with exemplary embodiments of the present invention.

DETAILED DESCRIPTION OF THE INVENTION

The present invention generally relates to systems, methods, and program products for providing and administering a digital asset network with rapid transaction settlements. The present invention uses a cooperative network of computing nodes, including super peer computing nodes, to govern a trustless digital asset system. At any given time a configuration agent schedules a single super peer computing node to perform minting or mining operations, which include transaction confirmations. This single minting software agent can provide immediate or rapid verification of transactions and thus rapid settlement. Since only a single super peer is performing the duty of confirming transactions at any one time, there are never the possibilities of orphan transactions or orphan blocks since there is no potential for competing blockchains or distributed ledgers. There is also no risk of double spending transactions. The cooperative yet trustless system of the present invention is key to providing these benefits while maintaining a secure distributed digital asset network.

In embodiments, consensus, which may be achieved by stake-weighted voting, may be primarily required when misbehavior is detected. The method may be resistant to adversaries lacking sufficient stake. A faulty or misbehaving peer computer can be disconnected from the network by a quorum of its stake-weighted peer computers.

Figure 1A:
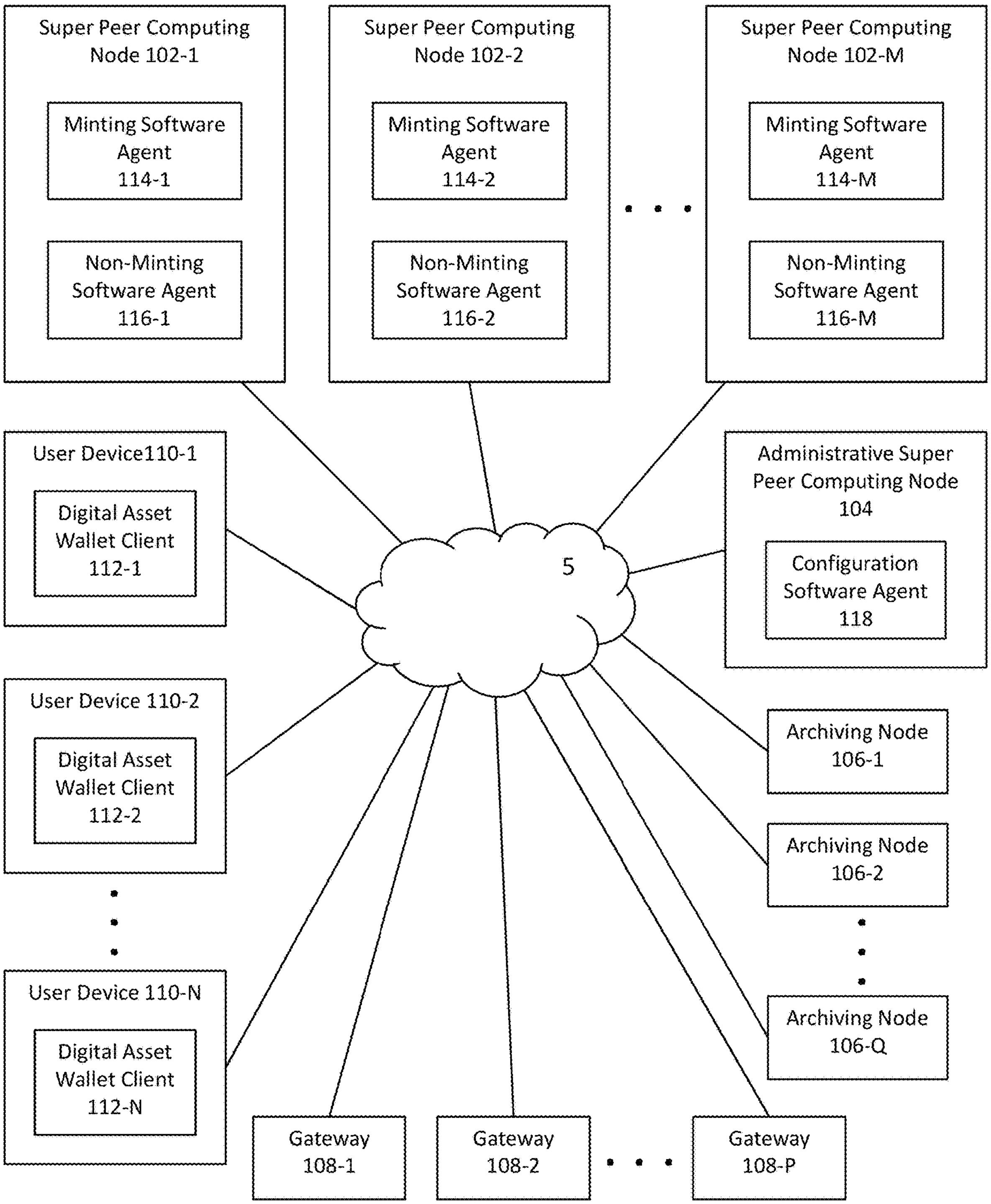
FIG. 1A is a schematic diagram of participant nodes in a digital asset network in accordance with exemplary embodiments of the present invention.

FIG. 1A is a schematic diagram of participant components, devices, and nodes in a digital asset network in accordance with exemplary embodiments of the present invention. The system may include one or more super peer computing nodes 102 (e.g., 102-1, 102-2, . . . 102-M), an administrative super peer computing node 104, one or more archiving nodes 106 (e.g., 106-1, 106-2, . . . 106-Q), one or more gateways 108 (e.g., 108-1, 108-2, . . . 108-P), and/or one or more user devices 110 (e.g., 110-1, 110-2, . . . 110-N).

The nodes in a digital asset system may comprise one or more computers. In embodiments, a node may comprise one or more servers. Each node may have one or more processors and non-transitory computer-readable memory, such as external and/or internal hard drives (e.g., hard disk memory, flash memory), disk drives, and/or other removable memory such as SD cards, memory cards, flash memory cards, and/or flash memory sticks. The nodes may further include data stored in one or more databases in the non-transitory computer-readable memory and/or one or more software modules stored in the non-transitory computer-readable memory and running or configured to run on the one or more processors. The nodes may include input devices (e.g., keyboards, mice, touchscreens, microphones, cameras) and/or output devices (e.g., display devices, speakers). The nodes may thus have respective interface modules configured to generate or update user interfaces or to generate and/or transmit machine-readable instructions to be used to generate and/or update graphical user interfaces at one or more nodes.

In embodiments, a node may store any of one or more local copies of a distributed electronic ledger, one or more local copies of a portion of a distributed electronic ledger, or one or more tamper-evident electronic logs, to name a few. For example, different software agents configured on a single node may each maintain its own electronic log. In embodiments, a node such as a gateway node 108 may store no such data. In embodiments, a node or user device may be associated with a digital asset address. Each node may have a respective digital asset address. In embodiments, a node may be associated with a plurality of digital asset addresses, such as for different digital asset accounts. A node may be associated with user identification information, such as user account information, anti-money laundering information, know your customer information, to name a few. In embodiments, each digital asset address may be associated with such user account information. In embodiments, a node may store respective asymmetric key pairs (e.g., a private key and a corresponding public key) used to provide a respective digital signature. In embodiments, a node may store public keys associated with one or more other nodes. A node may be configured to run a cryptography module to generate hashes of data, e.g., using a SHA-256 hashing algorithm or another hashing algorithm.

The nodes in a digital asset system may be operatively connected directly, such as via wired or wireless communications, and/or indirectly, such as via a data network 5, such as the Internet, a telephone network, a mobile broadband network (e.g., a cellular data network), a mesh network, a local area network (LAN) (including a wireless local area network, e.g., a Wi-Fi network), a wide area network (WAN), a metropolitan area network (MAN), and/or a global area network (GAN), to name a few. Data networks may be provided via wired and/or wireless connections. Data networks may be public or private. Accordingly, data networks may be open or closed, such as requiring authorized access, specific communication connections, or specialized hardware and/or software. In embodiments, any combination of communications channels may be utilized by the nodes. The nodes may each include one or more communications portals, which may handle, process, support, and/or perform wired and/or wireless communications, such as transmitting and/or receiving data (e.g., data packets). In embodiments, transmission described with respect to a single data packet may comprise a plurality of data packets. Data packets may be discrete electronic units of data. In other embodiments, transmissions may comprise non-discrete signals, such as data streams. Transmissions described with respect to data packets may also comprise data transmissions via other communications mechanisms known in the art, such as data streams. Communications portals can comprise hardware (e.g., hardware for wired and/or wireless connections, such as communications chipsets, communications interfaces, and/or communications antennas, to name a few) and/or software.

Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Wired connections may be provided through telephone ports, Ethernet ports, USB ports, and/or other data ports, such as Apple 30-pin connector ports or Apple Lightning connector ports, to name a few. Wireless connections may include cellular or cellular data connections and protocols (e.g., digital cellular, PCS, CDPD, GPRS, EDGE, CDMA2000, 1×RTT, Ev-DO, HSPA, UMTS, 3G, 4G, 5G, and/or LTE, to name a few), Bluetooth, Bluetooth Low Energy, Wi-Fi, radio, satellite, infrared connections, ZigBee communication protocols, to name a few. Communications interface hardware and/or software, which may be used to communicate over wired and/or wireless connections, may comprise Ethernet interfaces (e.g., supporting a TCP/IP stack), X.25 interfaces, T1 interfaces, and/or antennas, to name a few.

In embodiments, communications may be encrypted and/or authenticated. For example, messages may be encoded by TLS v1.2 and/or may contain a digital signature associated with the sending agent or node. A communication endpoint may have a unique certificate, such as an X.509 certificate. Each communication endpoint may verify the credentials of the other endpoint. In embodiments, a central certificate authority may not be required, as software agents may generate their own unique, self-signed X.509 certificates.

In embodiments, each super peer computing node 102 may comprise one or more software agents, such as a respective minting software agent 114 and/or a respective non-minting software agent 116. These software agents may be activated and/or deactivated according to a schedule provided by and/or machine-readable instructions provided by a configuration software agent 118. The minting software agent 114 may perform minting operations, such as to confirm digital asset transactions and/or mint new digital assets, as described herein. In embodiments, The non-minting software agent 116 may perform non-minting operations associated with management of and/or provision of a digital asset network, such as verifying the minting agent's confirmations of pending transactions, auditing neighboring nodes, and/or relaying data, to name a few, as described herein. In embodiments, each non-minting agent may audit and/or verify the work of the minting agent and/or of other non-minting agents, as described herein. The super peer computing nodes 102 may have high processing power and/or may be connected to each other and/or to non-super peers via high bandwidth connections.

In embodiments, the administrative super peer computing node 104 may comprise a configuration software agent 118. The configuration software agent 118 may govern scheduling of roles for the super peer computing nodes 102. During any given period of time, the configuration software agent 118 may designate exactly one super peer computing node 102 to run its respective minting agent 114. The other super peer computing nodes 102 may run non-minting software agents 116 during that period of time, e.g., according to instructions from the configuration software agent 118. In embodiments, the administrative node 104 may not be a super peer computing node. The administrative node 104 may also run a network operations agent, which may monitor network activity (e.g., data flows, connectivity, exceptions, errors, system-generated messages, to name a few). In embodiments, a network operations agent may generate, transmit, and/or display an electronic message for system administrators, such as in the event an error occurs or a tamper is detected. The network operations agent may automatically reconfigure nodes in the network (e.g., the network node architecture) based upon events such as dropped connections, weak connections, attacked nodes, otherwise unavailable nodes, or nodes with higher availability or unused processing capabilities, to name a few.

Archiving nodes 106 may be full nodes that have a complete copy of a digital asset distributed electronic ledger. In embodiments, each archiving node 106 may receive updates to the digital asset distributed electronic ledger, which may be a new portion of the ledger, e.g., new blocks to a blockchain, and may store the updated ledger. The archiving nodes 106 may store the ledger in respective non-transitory computer readable memory, such as disk memory. In embodiments, archiving nodes 106 may relay digital asset data, such as ledger data, to other nodes including other archiving nodes 106 in the digital asset network. The archiving nodes 106, which are non-super peer nodes, can perform verification of received transactions and of received electronic ledger portions, e.g., blocks of a blockchain. The archiving nodes may confirm that a hash value of a local copy of the distributed electronic public ledger matches a hash value of the canonical version of the distributed electronic ledger created by the minting agent.

User devices 110 may be computers, desktop computers, laptop computers, tablet computers, handheld computers, wearable computing devices, smart phones, cell phones, personal digital assistants, and/or transaction kiosks, to name a few. User devices 110 may run software configured to participate in the digital asset network, such as by performing digital asset transactions. Such software may be an instance of a digital asset wallet client 112. In embodiments, a financial institution machine trading computer system may be a user device that sends transaction data to a gateway 108 and/or receives transaction data from a gateway 108.

Gateway nodes 108 may be access points used by wallet nodes or other full nodes to communicate (e.g., transmit and/or receive data) with a digital asset network, such as other nodes in a digital asset network. For example, a wallet client 112 running on a user device 110 may transmit digital asset transaction details or parameters to one or more gateways 108, which may be nearby gateways. The gateways 108 may relay the data to one or more super peer computing nodes 102. The gateways 108 comprise one or more servers, which may be robust and/or secure access points, designed to be resistant to attacks, such as distributed denial of service attacks.

Figure 1B:
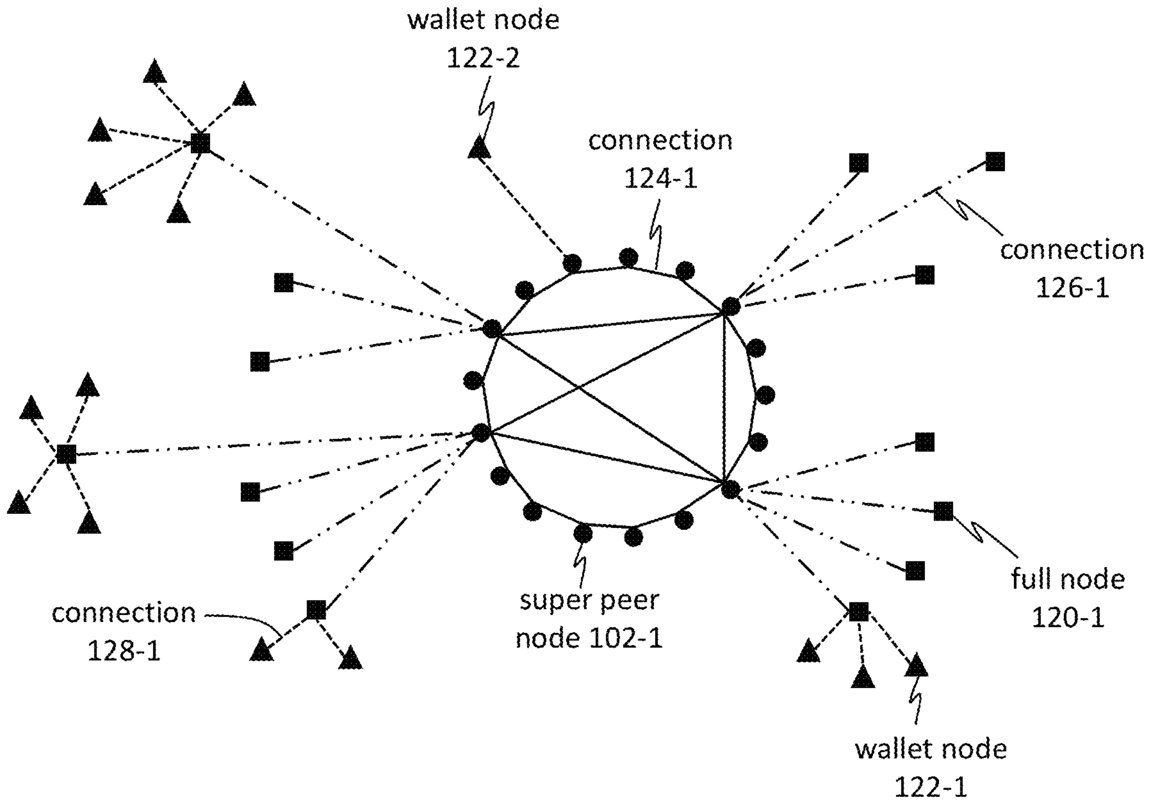
FIGS. 1B-C are schematic diagrams of exemplary digital asset network architectures in accordance with exemplary embodiments of the present invention.
Figure 1C:
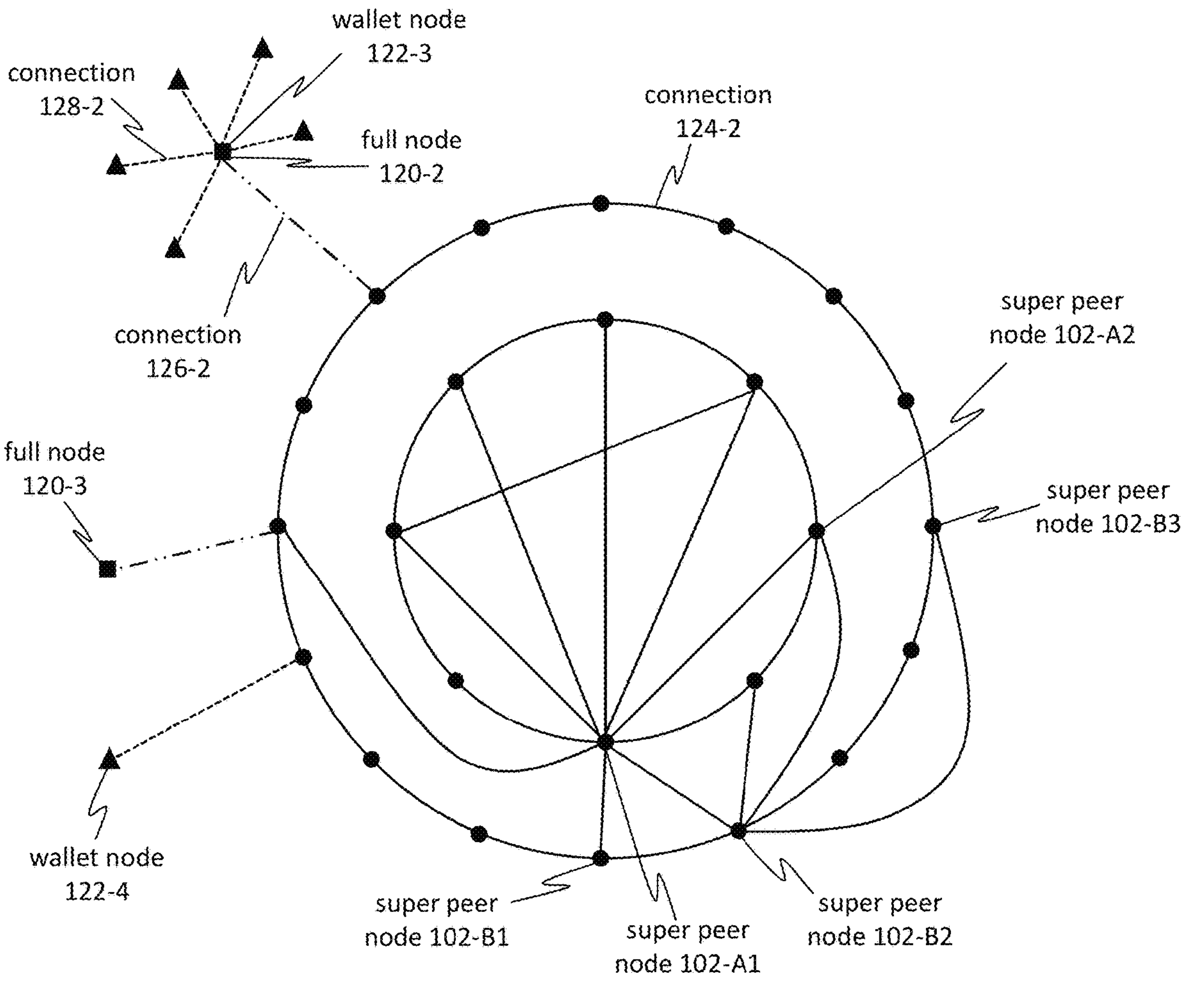

FIGS. 1B-C are schematic diagrams of exemplary digital asset network architectures in accordance with exemplary embodiments of the present invention. FIG. 1B shows an architecture with an inner network of super peer computing nodes 102. The nodes may be connected directly via connections 124, such as via high bandwidth wired connections. In embodiments, the nodes may be connected indirectly, such as through a data network. In embodiments, each super peer computing node 102 may be connected to each other super peer computing node 102. The administrative node 104 may also be connected to each super peer computing node 102.

The super peer computing nodes 102 may be connected to full nodes 120 via respective connections 126, which may be high availability spokes. In embodiments, connections 126 may not be as fast or capable of carrying as much data as connections 124. In embodiments, each node can have multiple connections to super peers carrying redundant messages, such as for fault tolerance and/or misbehavior detection. Each super peer node 102 may be a hub for a plurality of full nodes 120. In embodiments, one or more nodes may be located in the same data center.

Full nodes 120 can include gateway nodes, archiving nodes, and/or other nodes maintaining full copies of the distributed electronic ledger. Other exemplary full nodes can be digital asset exchanges, payment processors, high frequency trading platforms, and/or digital asset indexing platforms (e.g., for computing and/or reporting digital asset prices, transaction data, and/or transaction statistics). In embodiments, full nodes may be wallets that originate transactions. In embodiments, gateway nodes may not be full nodes, as they may not maintain a copy of the ledger. In other embodiments, gateway nodes may be full nodes. Full nodes 120 may verify and/or replicate the distributed electronic ledger. Full nodes 120 may also relay transactions to one or more super peer computing nodes 102 to which they are connected.

Wallet nodes 122 may originate digital asset transactions. Wallet nodes, such as user devices running a wallet client, may connect to gateway nodes using a hub and spoke architecture, with the gateway being the hub. Wallet nodes may use connections 128, which may be consumer grade connections such as cellular data connections or consumer Internet connections, to name a few. Connections 128 may have lower capacity and/or transmission rates than connections 124. In embodiments, wallet nodes may connect directly to other wallet nodes, such as to relay transaction information to a gateway. Still in other embodiments, wallet nodes may connect directly to a super peer computing node, although it is preferred to use intermediate gateway nodes that can scrub traffic, aggregate communications, and/or provide resistance to attack.

Digital asset message traffic (e.g., transaction parameters) can originate in peripheral nodes, such as wallet nodes, and flow inward to the minting software agent. Acknowledged transactions and/or new blockchain hashes can flow outwards from the minting agent to blockchain-replicating full nodes and/or to wallet nodes beyond them.

The present invention may provide immediate or near-immediate transaction settlement. Pending transactions can be acknowledged by the minting agent. Software agents can intelligently route a new transaction directly from the issuer (e.g., the sending address) to the minting agent. Once the minting agent accepts the new transaction as pending, the minting agent can timestamp the transaction and broadcast its acceptance back to the network. Because the minting agent is located at the hub of a super peer network, outbound acceptances can be transmitted with low latency, to all archiving software agents, to customer wallets, to merchants, and/or to payment processors. In embodiments, the transaction can complete in less than one second.

In embodiments, transaction confirmations can replicated by other super peer nodes. Intelligent software agents can route new payment transactions to the designated nomadic mint, and may also in parallel send copies to a plurality of other super peer nodes. These backup super peer nodes may queue pending transactions and synchronize their states with the minting agent. If the primary minting agent fails, then a network operations software agent can conduct an election among the backups to choose the successor minting agent. In embodiments, a configuration agent may automatically select a next scheduled super peer computing node to replace the failed minting agent.

In embodiments, each transaction may be timestamped in a tamper-evident data structure associated with the blockchain and/or part of the blockchain. In embodiments, software agents can maintain a distributed data structure that contains additional information beyond the blockchain, such as a timestamp, customer accounting categorization, application-specific data, and/or encrypted data such as customer data.

Referring to FIG. 1C, an alternative architecture of an embodiment is shown, which uses concentric arrangements of super peer computing nodes 102. Such an architecture may enable larger scaling of the network to accommodate more transactions and/or to process transactions faster and/or more efficiently. The concentric ring architecture achieves the technical effect of reducing network congestion. In embodiments, multiple sets of concentric rings of nodes may be used. Nodes in an outer ring such as 102-B1, 102-B2, and 102-B3 may be connected to some or all of the nodes in the same ring. Such nodes may also be connected to some or all of the nodes in the next inner ring, such as super peer computing nodes 102-A1 or 102-A2. In embodiments, the nodes in the innermost ring may be directly connected to each other, whereas nodes in outer rings may be directly connected or indirectly connected to each other, such as through a data network. Nodes in the outer ring may be directly connected to at least some of the nodes in the inner ring to enable faster communication. Nodes in the outer ring may aggregate data and/or communications to transmit to nodes in the inner ring. Accordingly, those message sizes may be larger but transmitted less frequently, such as in bursts, which may reduce network congestion and/or increase processing efficiency. In embodiments with more than two concentric rings, some nodes in an outer ring may be connected to nodes in a ring that is more than one ring away.

Figure 1D:
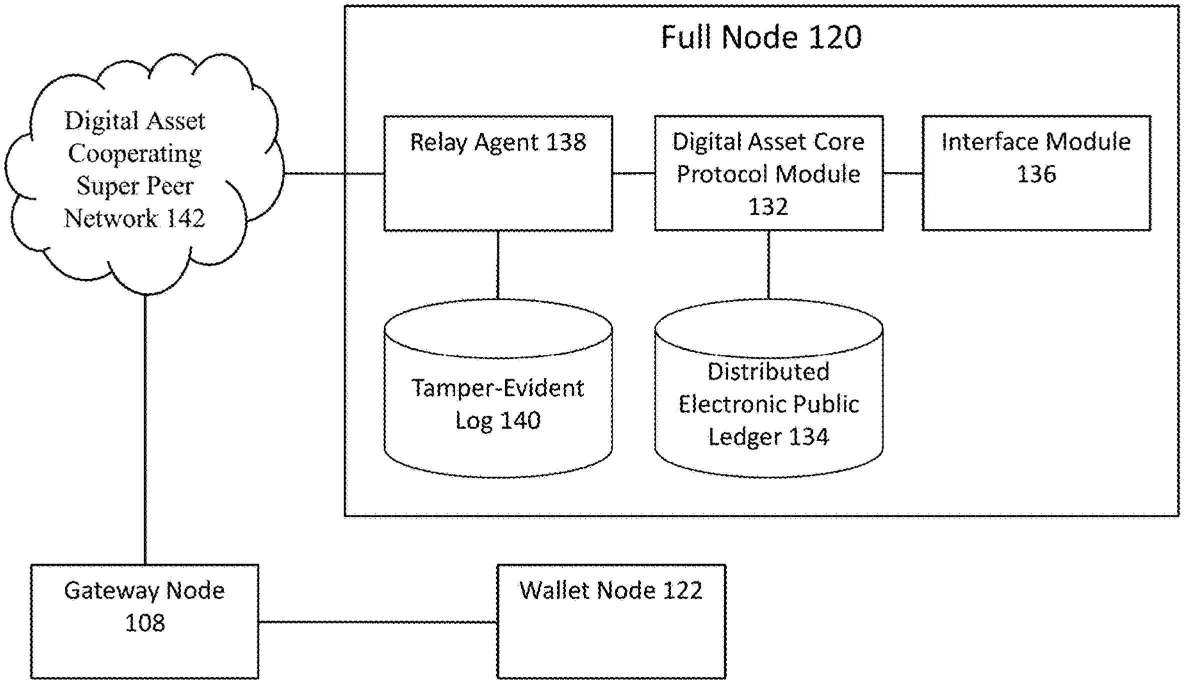
FIGS. 1D-F are schematic diagrams showing node architecture in accordance with exemplary embodiments of the present invention.
Figure 1E:
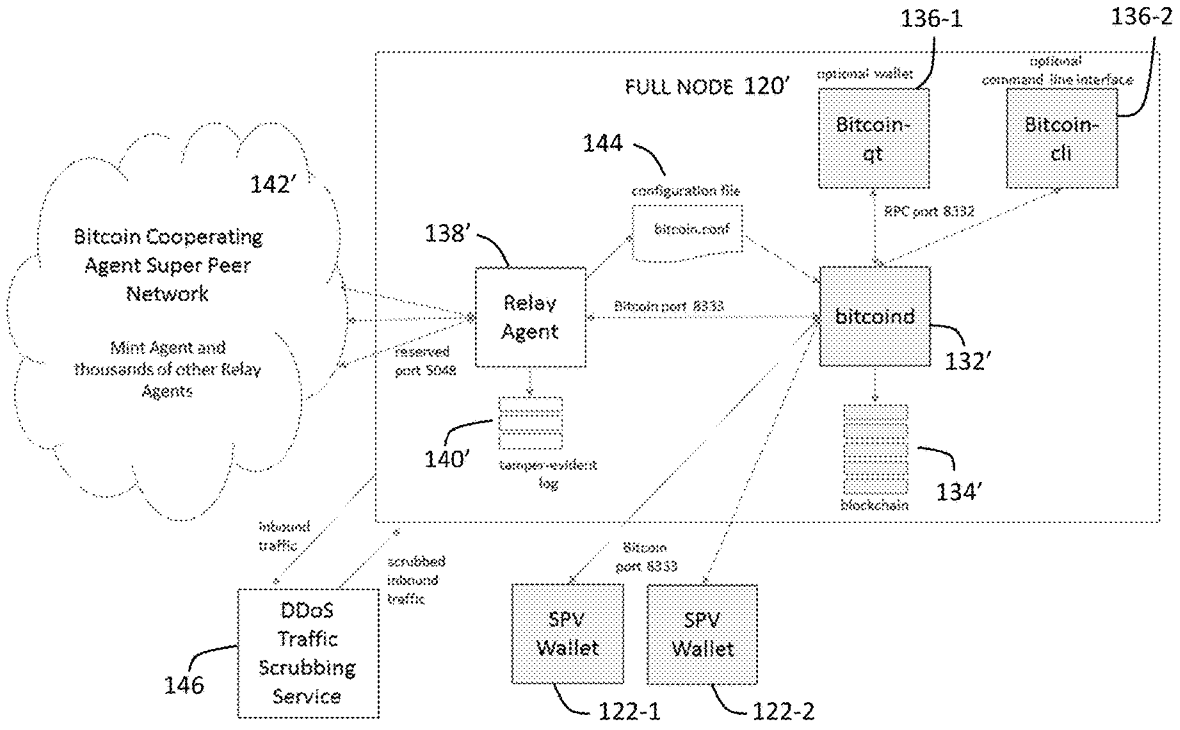
Figure 1F:
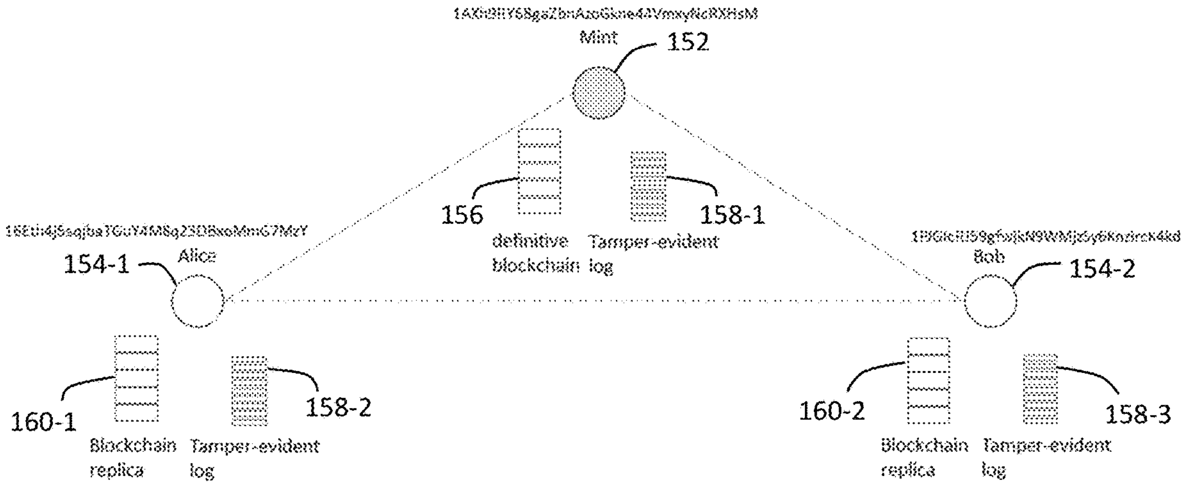

FIGS. 1D-F are schematic diagrams showing exemplary node architecture in accordance with exemplary embodiments of the present invention. FIG. 1D illustrates that the full node 120 can include an interface module 136 configured to provide one or more interfaces for participating in (e.g., transacting on) the digital asset network. Such interfaces can include wallet clients, graphical user interfaces, and/or command line interfaces, to name a few. A full node 120 may interact (e.g., communicate) with the digital asset cooperating super peer network 142 through a relay agent 138. The relay agent 138 may communicate directly and/or indirectly (e.g., via a data network) with one or more super peer computing nodes. On the other hand, one or more wallet nodes 122 may connect (directly or indirectly) to the super peer nodes through one or more gateway nodes 108.

In embodiments, the relay agent may be operatively connected to a tamper evident log 140, which may store all incoming and/or out-going data. The full node 120 may run a digital asset core protocol module 132, which may govern interaction in the digital asset network. For example, the core protocol module 132 may govern how the distributed electronic ledger is created, updated, and/or verified. Accordingly the core protocol module 132 may access and/or edit a local instance 134 of a distributed electronic public ledger. In embodiments, the tamper evident log 140 and the local instance 134 of the distributed electronic public ledger may be the same log (e.g., an immutable log, chained to previous log entries via a hash of data comprising a new log entry and the hash of the previous entry). In other embodiments, separate data structures may be maintained, as the tamper-evident logs may store more data than is necessary to provide a digital asset transaction log and thus could reduce performance to distribute the additional data throughout the network. The core protocol module 132 may also govern how communications including transaction information are structured. The core protocol module 132 may enable and/or dictate the parameters for transactions with multiple signatories, encrypted transmissions, and/or message signing using digital signatures, to name a few.

Digital asset transaction information can include associated sending and/or destination digital asset addresses, digital asset amounts (e.g., input amounts), account information associated with the sending and/or destination addresses, user identification information associated with the sending and/or destination addresses. In embodiments, user identification information may be transmitted along with transaction parameters. In other embodiments, user identification may be retrieved from a database, e.g., based upon a query comprising at least account information such as a digital asset address or other account number (e.g., a separate account number assigned to a user upon registering for participation in the digital asset network).

FIG. 1E illustrates an embodiment of the cooperative super peer digital asset network that modifies the Bitcoin system, e.g., via configuration file 144. Configuration file 144 may alter settings from the standard Bitcoin protocol in order to transform the system to a cooperative digital asset network instead of the adversarial network that is a defining feature of the Bitcoin system. The system may employ a modified version of proof of work, where a single super peer computing node is responsible for transaction confirmation without a computationally intense puzzle, and other nodes can verify the result. The system may use a modified version of the Bitcoin core protocol 132' (e.g., Bitcoin daemon), which has been configured and/or altered for participation in the cooperative network. Accordingly, a full node 120' may run this modified version of Bitcoin core 132'. The system may also use a version of the Bitcoin blockchain. However, the system may introduce electronic tamper-evident logs 140' with specific programming to store input data, output data, starting variable states, and/or ending variable states for each action taken by a node or each event (e.g., communication event) involving a node.

A relay agent 138' may be introduced to interface between the full nodes 120' and the network 142' of cooperating super peer computing nodes. The network 142' may comprise any number of nodes, such as tens, hundreds, or thousands, to name a few. Only one super peer node may perform minting operations at any given time, while the other super peer nodes and other full nodes may relay digital asset network communications, such as transaction information (transaction parameters and/or transaction confirmations) for pending digital asset transactions, ledger updates, tamper-evident log data, to name a few.

Wallet clients 122, such as simplified payment verification (SPV) wallets may communicate directly with a full node 120', which may be a gateway node. In embodiments, a communication scrubbing service 146 may be employed to filter, clean, and/or aggregate communications. SPV wallets may not maintain complete local copies of the public ledger but rather may rely upon full nodes to which they connect to ensure their lightweight summary of the public ledger is accurate.

A full node 120' may utilize interfaces such as a wallet interface 136-1 (e.g., Bitcoin-qt) and/or a command line interface 136-2 (e.g., Bitcoin-cli), which may be provided via the Bitcoin core protocol 132' but may display different data according to events and transactions on the cooperative network.

FIG. 1F illustrates a central trustless system in which a mint agent may create all new blocks, appended to a non-forking blockchain, on a fixed schedule. In embodiments, proof of work may not be required to achieve stability in the system. However, the system may suffer from centralization and/or lack of redundancy. These problems can be addressed by the system of the present invention, as illustrated, e.g., in FIG. 1B, and further described herein.

In the simplified centralized example of FIG. 1F, node 154-1 may prepare to pay node 154-2 with a new payment transaction. The tamper-evident log for node 154-1 may record the issuance activity details that include the local timestamp, the digital virtual currency transaction, and the connection endpoint's, e.g. the mint's, coin address. The transaction to be sent can be packaged with the transaction details, and an authenticated hash of the tamper-evident log of node 154-1. In embodiments, the transaction may be sent directly to the connected mint agent 152.

In embodiments, the mint agent 152 may directly receive the transaction and can log its arrival. The mint agent can immediately send back to node 154-1 an authenticated hash of its own tamper-evident log containing the transaction. At this point the tamper-evident logs of node 154-1 and the mint agent 152 may be considered entangled. Despite differences in their respective local clocks, the temporal order of the distributed process steps can be verified by any observer querying the logs. Node 154-1 knows that the mint agent 152 received the transaction.

The mint agent 152 can validate the transaction. If invalid, an invalid status may be logged and sent back to originating node 154-1. Otherwise, the transaction is a candidate for inclusion into a new block. If there is no transaction fee, the transaction may be accepted according to a rule that permits a certain percentage of free transactions per block. If rejected by that rule, that status is logged and it is sent back to node 154-1. Otherwise the mint logs the accepted transaction status.

The mint agent 152 may broadcast the accepted transactions directly to its peers, namely nodes 154-1 and 154-2. Node 154-2 may immediately know that the payment from node 154-1 will be included in the next block created by the mint agent 152 with trivial proof of work at an exact predefined interval, e.g., a 10-minute interval. In embodiments, when the mint agent 152 creates the new block, it can keep a certain portion of the block reward and transaction fees for itself, and can pay the remainder daily to nodes 154-1 and 154-2 as immediately spendable dividends in proportion to their offered stakes. Nodes 154-1 and 154-2 can both log the acknowledged transaction, and may verify the work of the mint by building their own new block using the same inputs in the same timestamped order as the mint. Tamper-evident logs from node 154-1 (log 158-2), the mint 152 (log 158-1), and node 154-2 (log 158-3) permit each of these participants to prove that they behaved correctly. Each participant can identify itself by a certain digital asset address that they respectively control. The private key of the address can be used to digitally sign certain messages and/or to verify that responses were sent by the intended recipient.

Because there is a single mint, there may be no need for a proof of work. The tamper-evident logs may facilitate remote attestation of correct peer computer behavior. The identity of nodes 154-1 and 154-2 can be supported by their respective stakes. When there is a need for a consensus, votes can be tallied and weighted by offered states. Misbehaving computers can be banned from the network, thus strongly motivating honest behavior.

The system described with respect to FIG. 1F can be considered trustless because nodes can audit each other's tamper-evident logs to verify performance without having to trust the performing node. The system can be strengthened via a rotating minting agent that provides redundancy, geographic variation in the minting power, and/or variation in the ownership of the node performing the minting power. This rotating minting power is achieved through a configuration agent that schedules nodes to run a minting agent, one at a time.

Figure 2:
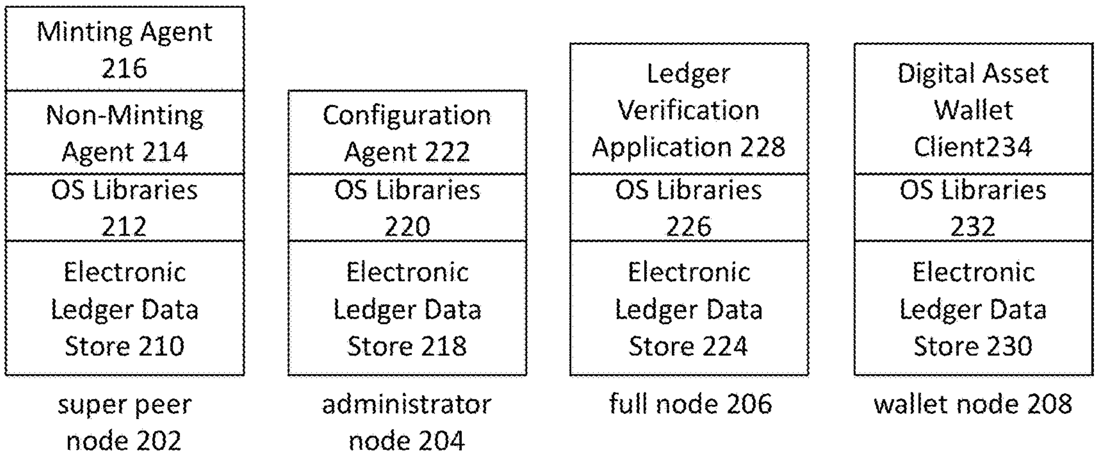
FIG. 2 is a schematic diagram of exemplary software stacks of nodes in a digital asset network in accordance with exemplary embodiments of the present invention.

FIG. 2 is a schematic diagram of exemplary software stacks of nodes in a digital asset network in accordance with exemplary embodiments of the present invention. Each node may maintain a respective electronic ledger data store, which may be a data volume comprising public ledger data. The public ledger may be an append-only store of transaction data. It may be made tamper-evident via a chain of hash codes of data within the ledger. Each node may also maintain respective operating system (OS) libraries. The operating system libraries may be the computer operating system and/or required software libraries that support the agent network.

The software stack for a super peer node 202 may comprise an electronic ledger data store 210 and operating system libraries 212. The stack may further include a non-minting agent 214 and a minting agent 216, as described herein. The minting agent 216 is a software agent that has the sole responsibility for accepting transactions (confirming transactions) and periodically storing transactions in the electronic ledger data store 210. The behavior of the minting agent (e.g., inputs, outputs, variable values before and/or after processing, processing statistics or information) may be recorded in a respective tamper-evident log, e.g., stored within minting agent memory. The non-minting agent 214 may be one or more software agents that verify the correct behavior of the current minting agent (e.g., by evaluating pending transactions to verify them independently and/or by re-computing electronic ledger portions to compare against master electronic ledger portions created by the minting agent. The non-minting agent 214 may also maintain replica copies of the minting agent's electronic ledger data store. The behavior of the non-minting agent 214 may be recorded in a respective tamper-evident log, which may be stored within the non-minting agent memory or memory otherwise operatively connected to the non-minting agent. In embodiments, additional agents may implement the configuration established by a configuration agent and may implement network settings.

The software stack for an administrator node 204 may comprise an electronic ledger data store 218 and operating system libraries 220. The administrator node 204 may further comprise a configuration agent 222, which may schedule minting and non-minting operations among the super peer nodes, as described herein. In embodiments, the configuration agent 222 may schedule a rotation of minting roles among some or all of the super peer computing nodes. In any given period of time the configuration agent 222 may schedule only one singleton minting agent. The configuration agent 222 may distribute a schedule in advance, may transmit machine-readable instructions comprising role scheduling information at or just prior to a time when a role change is to take effect, and/or may transmit instructions for deviations from or changes in an existing schedule. In embodiments, a current schedule may be provided by the configuration node and stored at the other nodes. In embodiments, no schedule may be stored, and role changes may take effect upon receipt of scheduling instructions from the configuration node. The behavior of the configuration agent 222 may be recorded in a respective tamper-evident log stored in memory of the configuration agent 222.

The software stack for a full node 206 may comprise an electronic ledger data store 224 and operating system libraries 226. The full node 206 may further include a ledger verification application 228 to calculate independent instances of updates to the public electronic ledger and compare them against a main copy of the public electronic ledger disseminated from the minting agent during a given time period. A ledger verification application 228 may verify transactions and additions to the electronic ledger data store (e.g., receiving updates to the electronic ledger data store from the minting agent and comparing such updates against its own computations regarding the electronic ledger data store). There may be numerous full nodes 206 in the digital asset network with geographic distribution, providing a robust archive of the electronic ledger data store. The ledger verification application 228 may be an agent, and its behavior may be recorded in a respective tamper-evident log stored within the memory of the agent.

The software stack for a wallet node may comprise an electronic ledger data store 230 and operating system libraries 232 (e.g., personal computer operating system libraries, smart phone OS libraries such as Android implementations or iOS implementations, to name a few). The wallet stack may further comprise a digital asset wallet client 234, which may be configured to authenticate users (e.g., via communications with an authentication module running on a server and/or via comparison against locally stored reference user credentials), perform transactions (e.g., send and/or receive digital asset payments from other accounts in the digital asset network), display the results of transactions (e.g., transaction confirmation, transaction rejection), display account balances, and/or display a transaction history, to name a few. The digital asset wallet client 234 may be the user interface for accessing and/or transacting with the digital asset.

Figure 3:
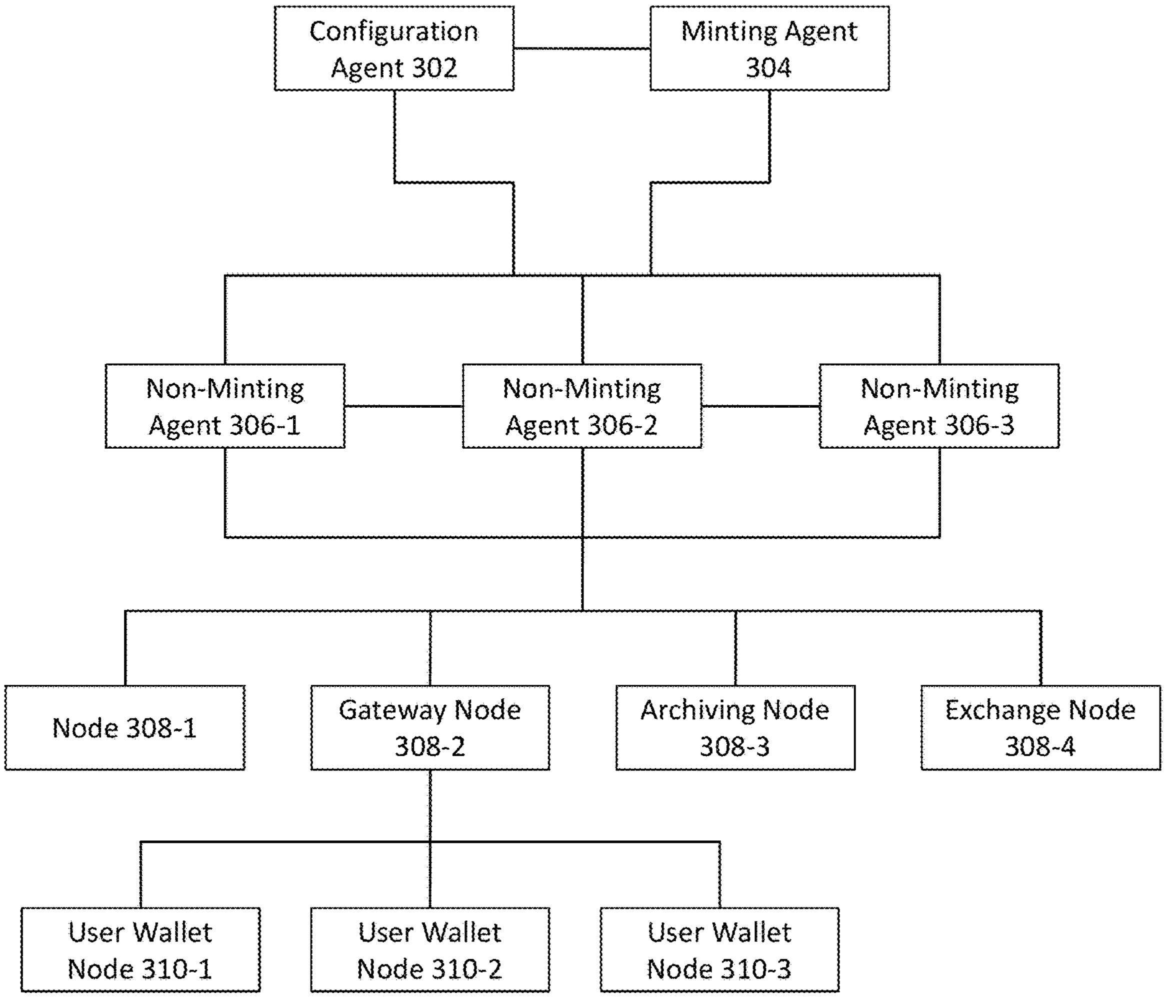
FIG. 3 is a schematic diagram showing logical topology in a digital asset network in accordance with exemplary embodiments of the present invention.

FIG. 3 is a schematic diagram showing logical topology in a digital asset network in accordance with exemplary embodiments of the present invention. The logical topology is based on a relatively fixed arrangement of logical roles, but the logical subordination of nodes is configurable such that at a first time a first node may perform logical role A (e.g., minting, which entails transaction confirmations) and at a second time a second node may perform the logical role A while the first node performs a different logical role B.

In embodiments, agents may be organized into a hierarchical control network in which each agent in the hierarchy is a linked node in a tree. Commands, tasks, and/or goals to be achieved may flow down the tree from superior agents to subordinate agents, whereas input data, sensations, and/or command results may flow up the tree from subordinate to superior agent. In embodiments, each layer of the hierarchy can operate with a longer interval of planning and execution time than its immediately lower layer. The lower layers may have local tasks, goals, and/or sensations, and their activities may be planned and/or coordinated by higher layers.

A top node, which may be a governance node, followed by a network operations node may exist at the top of the logical hierarchy. Each node below the governance node may have a governance sub-agent to ensure that governance is maintained and/or executed according to machine-readable instructions from the governance node. Governance agents can ensure that each node's agents are complying with network policy, e.g. no fatal software exceptions, no alteration of tamper-evident logs, etc. The network layer of the hierarchy may manage the entire network, such as by intelligently routing transactions, facilitating connection of new nodes into the network, seeding new nodes with data, scheduling agent locations (e.g., for a nomadic agent that moves locations, such as a mobile device or smart phone or for nomadic role, such as a nomadic minting agent where minting operations are performed by different nodes at different times), and/or detecting and/or automatically responding to software and/or communications faults, to name a few. In embodiments, the network layer may conduct elections among super peer nodes to replace a failing peer node, such as a node that is not processing efficiently or is processing too slowly. In embodiments the network layer may be responsible for deploying new versions of software and/or data. It may have the power to restart the network. The network layer may also copy local tamper-evident log files for automated remote analysis.

However, as pertains to the digital asset processing aspect of the architecture, a configuration agent 302 may be at the top level. The configuration agent may designate roles for super peer computing nodes. Each other node may have a configuration sub-agent that is subordinate to the configuration agent 302. The configuration sub-agents may execute behavior based on messages received from the configuration agent 302, such as to implement the assigned roles. In embodiments, wallet nodes may not run a configuration sub-agent.

The configuration agent 302 may assign a particular super peer computing node to run its minting agent 304 to perform minting operations for the digital asset network. In embodiments, no nodes may report to the minting agent 304. The minting agent 304 may occupy an upper level in the logical hierarchy because its copy of the distributed electronic public ledger is considered the master copy of the ledger and because the minting agent confirms transactions for immediate settlement.

The single minting agent at any given time, hosted by a super peer computing node, may have the responsibility of creating new blocks and/or minting new digital assets. New block creation can be synchronous, using a predefined consensus timestamp, such as at the hour, 10 minutes past the hour, 20 minutes past the hour, etc., at the rate of six blocks per hour. In embodiments, other frequencies and/or times of day may be selected and programed into the minting protocol. Received transactions may be immediately broadcast back into the network with the acknowledged arrival timestamp so that some or even all peer computers may build the new block in synchronization with the minting agent.

When the issuing computer or device associated with the sending digital asset address receives the acknowledged transaction, it may indicate to the user that the transaction is acknowledged, which may be an indication that the transaction is confirmed. The transaction may not yet be committed into the blockchain. After aggregating new transactions for a predetermine period of time, e.g., 10 minutes, the minting agent may create a new block and link it into its blockchain. It can broadcast a resulting new hash to all peer computers, who can confirm it against their respective replica blockchains. In embodiments, discrepancies may be reported to an audit agent. In embodiments, ledger portions or blocks may have a maximum block size. Transactions that arrive after the maximum block size is reached can be processed into the following ledger update cycle. In embodiments, the minting agent may perform merged mining on behalf of a plurality of digital assets configured or re-configured for compatibility with the cooperative super peer system of the present invention.

The configuration agent 302 may assign others of the super peer computing nodes to run respective non-minting agents 306. In embodiments, non-minting agents may be run by default when a super peer node is not designated as the minting node.

Outside of the super peer nodes, full nodes may participate in the digital asset network to relay communications (e.g., transaction data), verify activities of other nodes, and/or archive copies of the distributed ledger. A node 308-1 may be a full node participating in the network. It may originate transactions. A gateway node 308-2 may be configured to serve as an access point to the super peer network and/or to provide security for the super peer network. An archiving node 308-3 may archive the distributed ledger, which in embodiments may be a function performed by all full nodes. An exchange node 308-4 may be a digital asset exchange that provides a trading platform to exchange digital assets for other types of digital assets and/or for fiat currency.

User wallet nodes 310 may be the lowest level of the logical hierarchy. Wallet nodes 310 may originate transactions, transmitting transaction parameters (e.g., digital asset amounts, sending account addresses, destination account addresses, transaction timestamps, customer identification information, to name a few) to one or more gateway nodes 308-2 for broadcast and/or transmission to other nodes in the digital asset network, e.g., for confirmation so that the transaction may be settled. Wallet nodes 310 may receive confirmations of settlement, which may be relayed through the one or more gateway nodes 308-2.

In embodiments, other agents may operate at nodes of the digital asset network. There may be numerous relay agents that can each manage an instance of the digital asset core protocol, e.g., in order to participate as a full node in the network.

In embodiments, a reward agent may distribute fees or dividends to super peer computer operators and/or others performing work for the digital asset network. Such fees may be paid periodically, e.g., daily, and/or may be paid when work is performed and/or in proportionate amounts to the number of transactions verified or to the values of the verified transactions. In embodiments, the reward agent may designate one or more destinations for unspent transaction outputs.

In embodiments, a financial controls and/or audit agent may ensure that the all peer agents are performing according to the required accounting policies. Tamper-evident records, e.g. the blockchain and logs of the agents, may be analyzed to verify that transactions correctly flow through the system, including block rewards.

In embodiments, a certificate authority agent may maintain a distributed repository of self-signed X.509 certificates for roles that require them. One agent may be identified as a certificate writer, and it may perform all updates to a canonical certificate repository on behalf of other agents. For example, an agent may create new X.509 certificates for its communicating roles and then send these certificates to the certificate authority agent to record in the repository. In embodiments, the certificate authority may broadcast the updates to all nodes or agents who can then update their local copies of the X.509 certificate repository.

In embodiments, a network deployment agent may coordinate with local agents to deploy new software and data versions and can restart the network if necessary.

Figure 4:
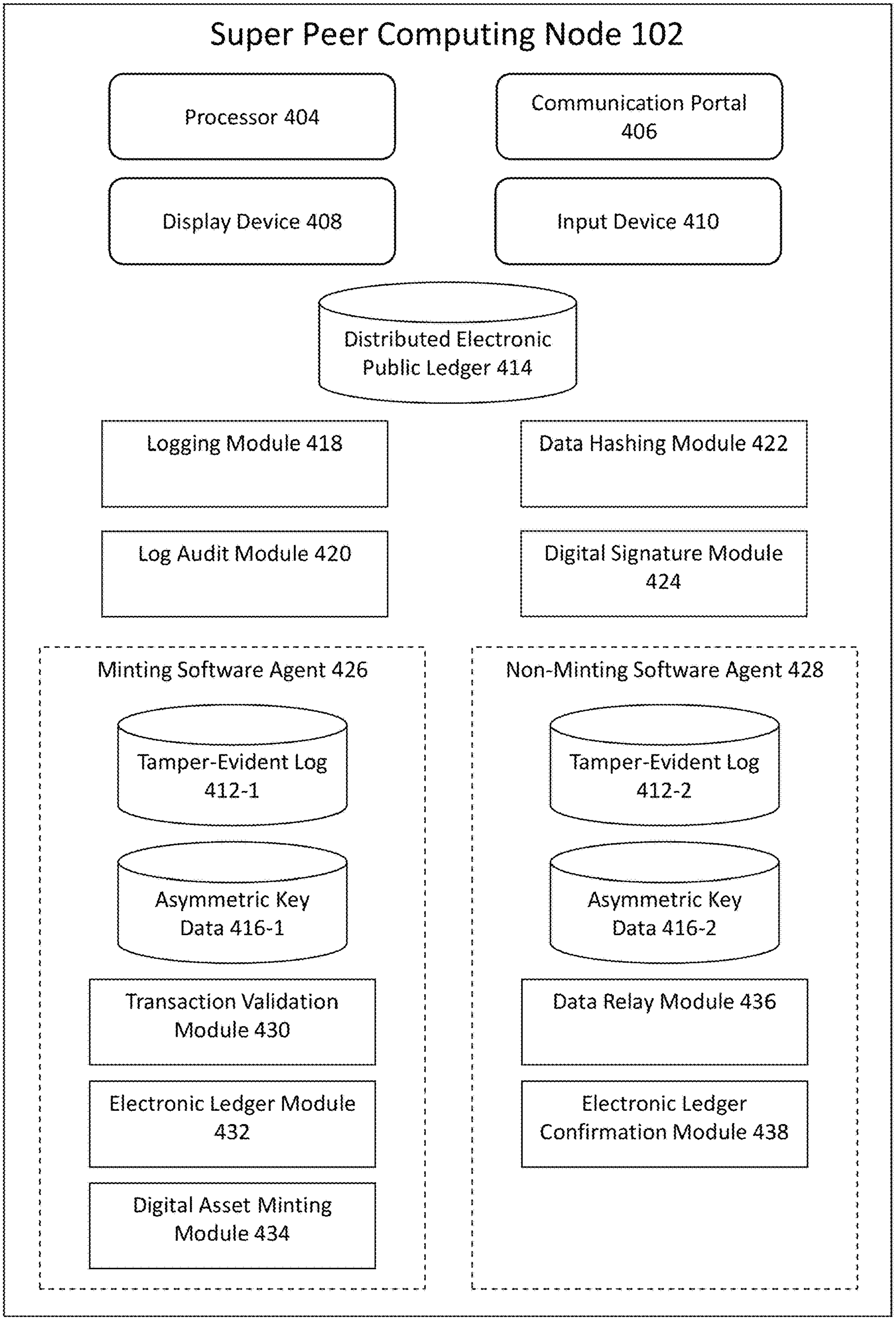
FIG. 4 is a schematic diagram of an exemplary super peer computing node in a digital asset network in accordance with exemplary embodiments of the present invention.

FIG. 4 is a schematic diagram of an exemplary super peer computing node in a digital asset network in accordance with exemplary embodiments of the present invention. The super peer computing node 102 can include one or more processors 404, communication portals 406, display devices 408, and/or input devices 410.

In embodiments, the super peer computing node 102 maintains a copy 414 of the distributed electronic public ledger. The super peer computing node 102 may also have one or more modules running and/or configured to run on the one or more processors 404. In embodiments, certain modules may be used by various agents running on the super peer computing node 102.

A logging module 418 may record in a respective tamper-evident log all transactions, events, input data, output data, beginning variable states, and/or ending variable states after processing. A log audit module 420 may verify the logs of other nodes in the network. It may insert an entry into logs of audited agents, thus entangling the logs.

A data hashing module 422 may generate hashes of data using one or more hashing algorithms, such as SHA-256. Hashes may be generated for insertion into logs and/or for encryption with a private key to produce a digital signature.

A digital signature module 424 may generate, sign, otherwise append, and/or transmit a digital signature, such as by computing a hash of data and encrypting the hashed data using a private key of an asymmetric key pair. In embodiments, the digital signature module 424 may decrypt and/or verify signed data, such as using a public key corresponding to the private key used to encrypt the data.

The super peer computing node 102 may be configured to run a minting software agent 426, which can perform minting operations as described herein. The minting software agent 426 may maintain its own tamper evident log 412-1 and have its own private key or asymmetric key pair 416-1. The minting software agent 426 can include a transaction validation module 430 to confirm pending digital asset transactions, an electronic ledger module 432 to update a copy of the distributed electronic public ledger, and/or a digital asset minting module 434 to generate new digital assets.

The super peer computing node 102 may be further configured to run a non-minting software agent 428, which may have its own tamper-evident log 412-2 and asymmetric key data 416-2. The non-minting software agent 428 may have a data relay module 436 to relay data to other nodes. It may further comprise an electronic ledger confirmation module 438 to generate its own updated ledger portions of a respective copy of the distributed ledger and compare them against the minting agent's updated ledger portions.

FIGS. 5A-C are schematic diagrams of exemplary tamper-evident logs in accordance with exemplary embodiments of the present invention. The present invention uses an attestable unforgeable log organization. In particular, this system can use attested append-only memory.

FIG. 5A illustrates a first agent's tamper-evident log 502-1. The log may comprise a plurality of log entries, e.g., entries 504-1 and 504-2. Each log entry may comprise log entry data 506, which can include the beginning states of relevant variables 510, any input data 512 (e.g., transaction parameters), process output indicators 516 (e.g., the results of processing, any output data, and/or any messages transmitted), a current timestamp 518, and/or a hash 520 of the previous log entry. That log entry data 506 along with a hash of the previous entry may then be hashed, e.g., using a SHA-256 hash algorithm, to generate a hash 508 of the log entry data, which is then inserted into the record. Because the previous hash (e.g., 508-1) is included in the current hash (e.g., 508-2), each successive log entry or record in the log is tied to the previous entries. In embodiments, the previous hash may not be included in the new hash.

FIG. 5B illustrates an alternative embodiment of a log, which shows that the hash 520 of the previous log entry need not be included in the log entry data 506' since a hash of the previous log entry is available in the prior log entry.

FIG. 5C illustrates an entangled log that has been audited by a second agent serving as an auditor. The log audit entry 504-4 can include log audit entry data 506-4, which may include a timestamp 520-1 from the auditor's remote computer system, an auditor digital signature 522-1, and/or a local timestamp 518-4 of the agent being audited. The log audit entry data 506-4 may be hashed (e.g., along with the previous entry hash) and inserted into the log. The log thus becomes entangled because an entry for a different agent, the auditing agent, has been inserted into it. The auditor agent may send a message to the audited agent requesting that its audit data be inserted into the audited log. In embodiments, the auditor digital signature may comprise a re-hash of the previous log entry hash, encrypted using a private key associated with the auditor.

A hash chain log may be a sequence of data records each including a field containing the hash digest of the previous record in the chain. If any log data in the chain is corrupted, the hash value of the corrupted records will fail verification. Because of the chained hash codes, the most recent log record's hash is sufficient to verify any record in the entire chain.

Action log entries, which can be used for action verification via replay, contain the context state that preceded the action, the inputs received from peers that affected the action, the action results, including the resulting new context state, and outputs sent to peer agents.

Peer agents can verify the actions of one or more observed peer agents by replaying the observed peers' tamper-evident logs. A verifying peer uses its own software to replay the log of an observed peer. If the log is verified, then the observed peer adds a log entry supplied by the verifying peer attesting to the correctness of the log at that point, resulting in log entanglement. If on the other hand, the replayed outputs do not match the observed outputs, then there has been a fault. Likewise there is a fault should ending context state disagree. When a fault is detected, a network operations agent may resolve the disagreement, either by a simple majority of verifying peers, or by a stake-weighted vote for relatively important disagreements, e.g. over the payment of rewards. In embodiments, faults within the network operations agent can cause its termination and super-peers may elect another one of their own as the successor by stake-weighted vote.

Each tamper-evident data structure, e.g. the action log, may be situated as a leaf in a network temporal hash tree. Each container is represented as a node in this tree, and its branches represent the tamper-evident hash chain links. A network root node is the parent of all containers. The network root hash is the hash function computed using the containers' hash value. In embodiments, at predefined intervals when a new block is created by the minting agent, the changed portion of the network hash structure is recomputed and archived. Therefore, the tamper-evident property of the blockchain, is extended to all verifiable data structures maintained by the software agents. Software agents in this invention are programmed such that they cannot lie about the contents of their action logs.

The network wide temporal hash tree, may be recomputed periodically, such as every 10 minutes. To anchor the hash tree root hash value in a timeline, a chaos value is added to each hash function input. In embodiments, this chaos value may be the integer daily solar flux value as reported by a certain astronomical observatory. Additional chaos indicators may be added to the root node of the hash tree, e.g. Bitcoin Blockchain hash value and most recent Bitcoin block height.

Certain tamper-evident data structures need to be searched for contents, which can be made easier by indexing the entries according to a key field value. The X.509 certificates are maintained as a distributed tamper-evident data structure which can be searched by qualified role name: <container-name>.<agent-name>.<role-name>.

Figure 6:
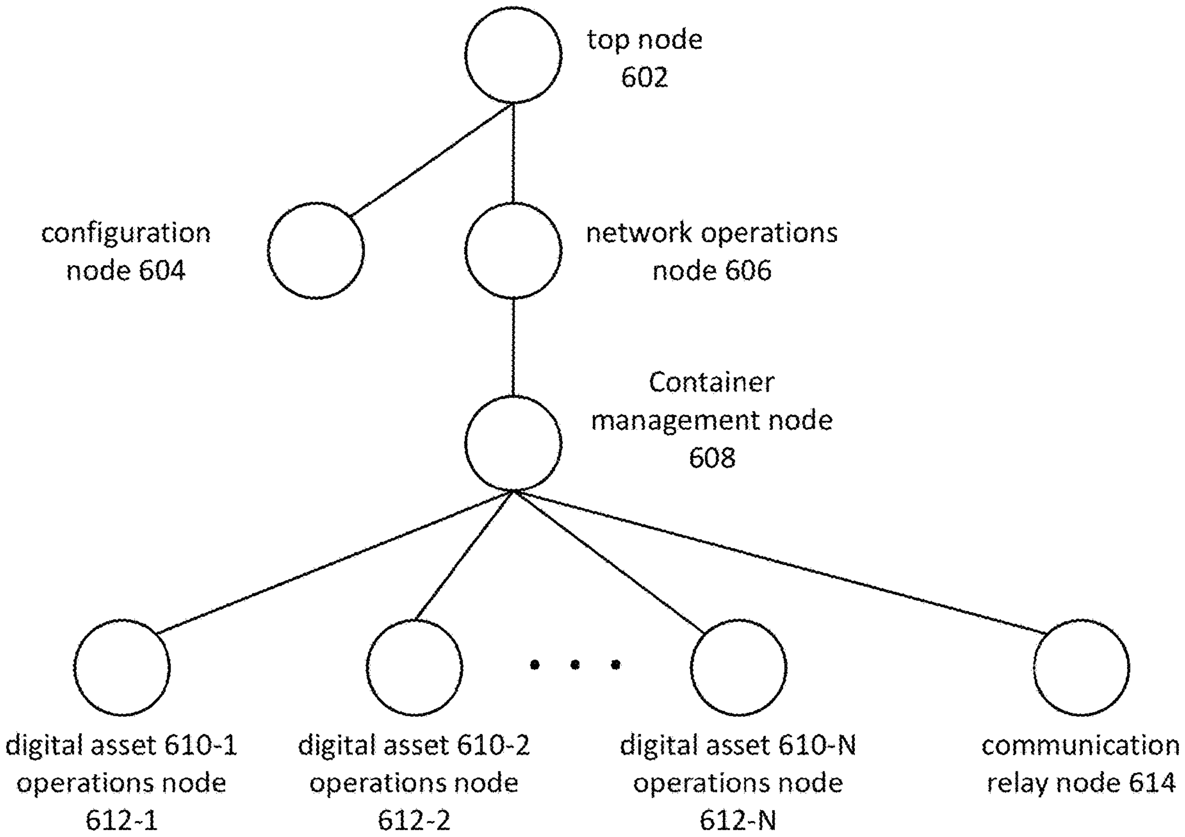
FIG. 6 is a schematic diagram of an exemplary network operations architecture in accordance with exemplary embodiments of the present invention.

FIG. 6 is a schematic diagram of an exemplary network operations architecture in accordance with exemplary embodiments of the present invention. A top node 602 may host a top agent, which may be the uppermost governance agent in the hierarchical control network of software agents. The governance agent may designate a position of each node in a logical hierarchical node-based architecture.

A network operations node 606 may host a network operations agent, which may manage the digital asset network, such as the network connectivity, communications pathways, load balancing, automatic reconfiguring, and/or network security.

A configuration node 604 may be an administrator node that hosts the configuration agent. The configuration agent may configure and schedule the roles played by agents hosted on the super peer nodes in the network.

A container management node 608 may manage containers, e.g., docker containers, and/or virtual machines, each of which may contain operating files required to establish a cooperative network of super peer computing nodes based on modifications that transform different underlying digital assets to the cooperative system and/or based on new types of digital assets. In embodiments, only a single type of digital asset may be provided. The container management node 608 may facilitate integration of the digital asset protocol and/or other required operations software with various hardware, operating systems, and/or operating system versions, such as Linux-based servers running varying Linux implementations.

One or more digital asset operations nodes (e.g., nodes 612-1, 612-2, . . . 612-N) may govern operation of respective digital assets (e.g., digital asset types 610-1, 610-2, . . . 610-N) within the cooperative super peer digital asset network. The operations nodes may reconfigure respectively programmed digital asset protocols to transform existing digital asset protocols to function in a cooperative proof of work system. In embodiments, the operations nodes may provide digital asset protocols for new digital assets 610 designed for use in the cooperative super peer system.

A communication relay node 614 may relay digital asset communications via one or more communications networks, such as the Tor network, and/or using one or more specific communications protocols. For example, a particular communications network may enable anonymous digital asset communications.

Figure 7A:
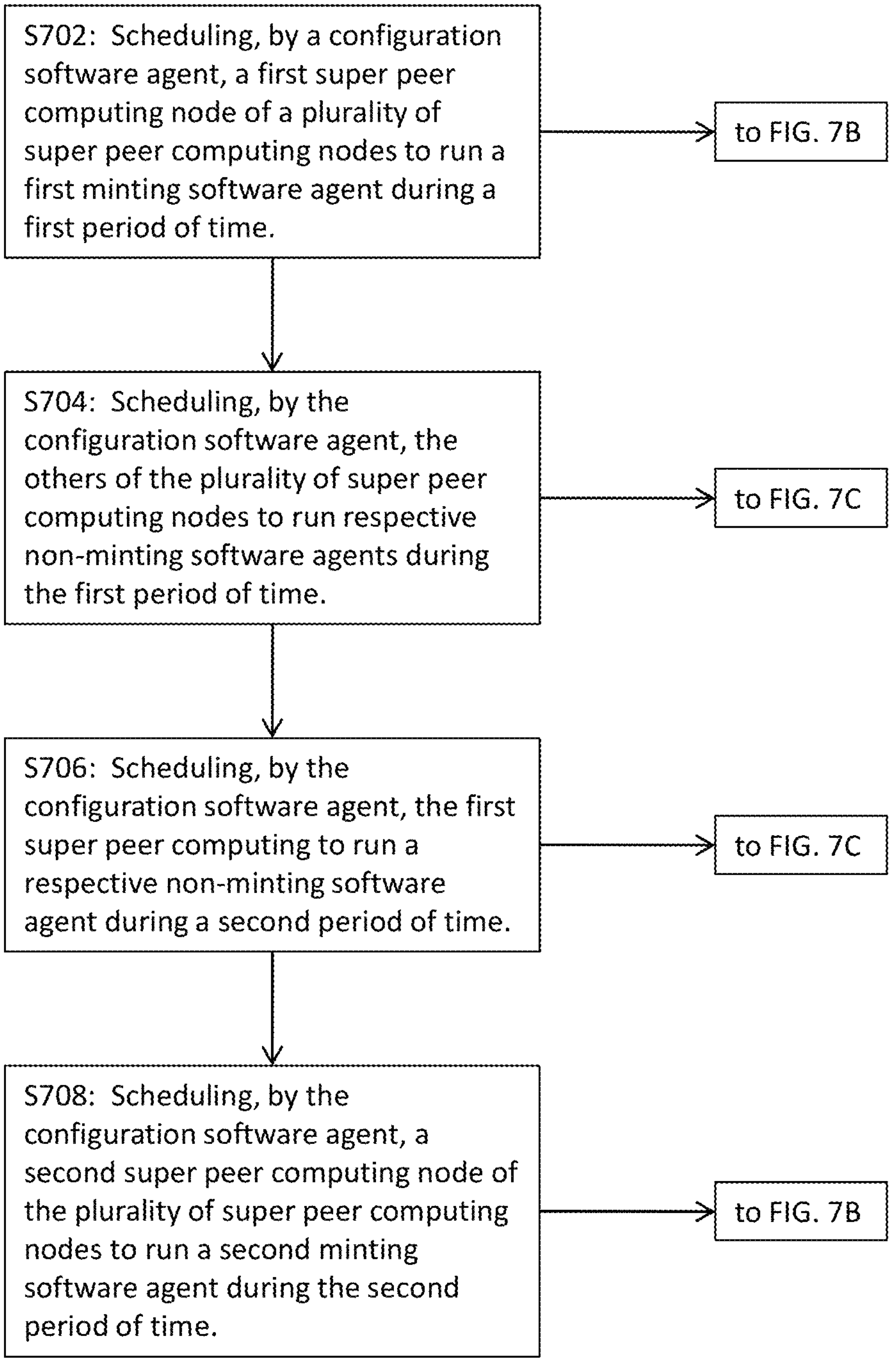
FIG. 7A is a flow chart of a configuration software agent scheduling mining control in accordance with exemplary embodiments of the present invention.

FIG. 7A is a representative flow chart of a configuration software agent scheduling minting control in accordance with exemplary embodiments of the present invention. For illustration purposes, Table 1 is referred to for a hypothetical scheduling sequence that could be employed in accordance with exemplary embodiments of the present invention:

TABLE 1

Example illustrating Scheduling of Minting Agents Among Super Peer Nodes

| Time Slot | Node A | Node B | Node C | Node D | Node E |
|---|---|---|---|---|---|
| 11:01 a.m. - 11:10 a.m. | minting | non-minting | non-minting | non-minting | non-minting |
| 11:11 a.m. - 11:20 a.m. | non-minting | minting | non-minting | non-minting | non-minting |
| 11:21 a.m. - 11:30 a.m. | non-minting | non-minting | minting | non-minting | non-minting |
| 11:31 a.m. - 11:40 a.m. | non-minting | non-minting | non-minting | minting | non-minting |
| 11:41 a.m. - 11:50 a.m. | non-minting | non-minting | non-minting | non-minting | minting |
| 11:51 a.m. - 12:00 p.m. | minting | non-minting | non-minting | non-minting | non-minting |

While this example illustrates an embodiment using five super peer nodes (Node A, Node B, Node C, Node D and Node E), there can be a larger number of super peer nodes, such as 7, 10, 20, 50, etc., to name a few or lesser number of super peer nodes, such as 3 or 4, used consistent with exemplary embodiments of the present invention. Further, while the Time Slots shown in Table 1, refer to 10 minute intervals starting at 11:01 a.m., other intervals could be used at other time slots consistent with the present invention. Further, while the scheduling order included in Table 1 provides a regular order in the assignment of the minting agent, other scheduling orders or random scheduling orders can be used consistent with exemplary embodiments of the present invention. Using this non-limiting example, the process set forth in FIG. 7A is discussed in detailed as follows.

In Step S702, the configuration software agent 118 schedules a first super peer computing node of a plurality of super peer computing nodes 102-1 to run a first minting software agent 114-1 during a first period of time. For example, referring to the example in Table 1 above, super peer computing node A may be assigned to be the minting agent during a first ten minute time interval from 11:01 a.m. to 11:10 a.m. As noted above, other durations and time periods could be selected consistent with exemplary embodiments of the present invention. As discussed below with respect to FIG. 7B, a more details explanation of these processes in accordance with exemplary embodiments of the present invention is set forth.

In Step S704, the configuration software agent 118 schedules, the others of the plurality of super peer computing nodes 102-1 to run respective non-minting software agents 116-1 during the first period of time. Referring again to the example in Table 1 above, during the same first time interval from 11:01 a.m. to 11:10 a.m., other super peer computing nodes B-E are assigned to be non-minting agents (or are not assigned to be minting agents and thus are not minting agents). Just as above, other durations and time periods could be selected consistent with exemplary embodiments of the present invention. Similarly, there may be fewer or greater number of super peer nodes participating in the system. As discussed below with respect to FIG. 7C, a more detailed explanation of these processes in accordance with exemplary embodiments of the present invention is set forth.

In Step S706, the configuration software agent 118 schedules the first super peer computing node 102-1 to run a respective non-minting software agent 116-1 during a second period of time. Again referring to the example from Table 1 above, in a second time interval from 11:11 a.m. to 11:20 a.m., super peer computing nodes A, C, D, and E may be assigned to be non-minting agents. In this time period, even though super peer computing node A was previously assigned to be a minting agent during the first time period, it is not assigned to be the minting agent during the second time period. In exemplary embodiments, the same super peer node may be assigned to be a minting agent during multiple consecutive time periods, as long as the minting agent is rotated during a plurality of time periods. Further, as previously noted, in exemplary embodiments, other durations and time periods could be selected. As discussed below with respect to FIG. 7C, a more details explanation of these processes in accordance with exemplary embodiments of the present invention is set forth.

In Step S708 the configuration software agent 118 schedules a second super peer computing node of the plurality of super peer computing nodes 102-2 to run a second minting software agent 114-2 during the second period of time. Again referring to the example from Table 1 above, in the second time interval from 11:11 a.m. to 11:20 a.m., super peer computing node B may be assigned to be the minting agent. In this embodiment, even though super peer computing node B was not assigned to be a minting agent in the first time interval (or was selected as a non-minting agent), in the second time interval it is instead selected to be the minting agent. In exemplary embodiments, the same super peer node may be assigned to be a minting agent during multiple consecutive time periods, as long as the minting agent is rotated during a plurality of time periods. Further, as previously noted, in exemplary embodiments, other durations and time periods could be selected. As discussed below with respect to FIG. 7B, a more detailed explanation of these processes in accordance with exemplary embodiments of the present invention is set forth.

Figure 7B:
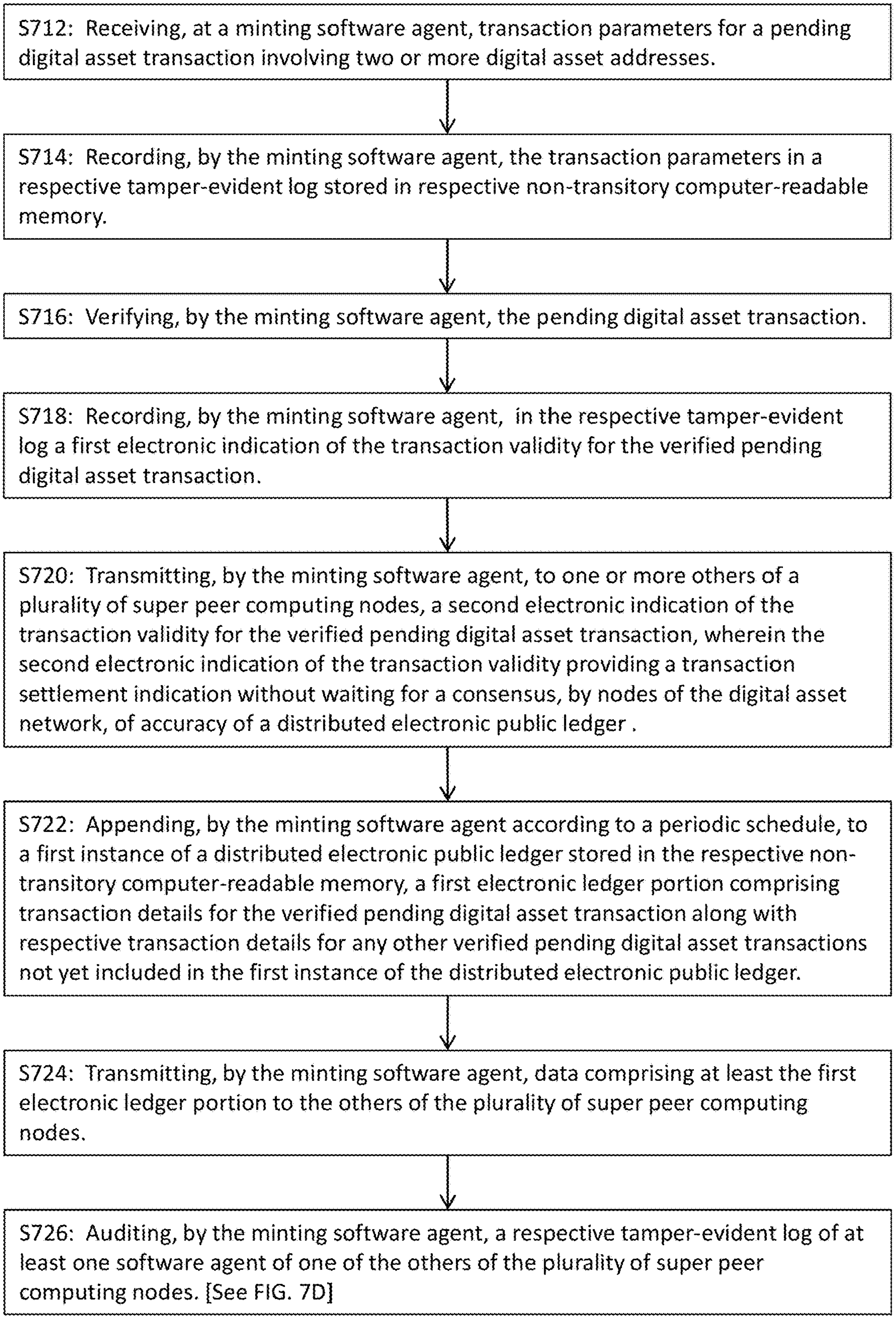
FIG. 7B is a flow chart of exemplary minting operations in accordance with exemplary embodiments of the present invention.

FIG. 7B is a flow chart of exemplary minting operations in accordance with exemplary embodiments of the present invention. Such minting operations may be performed as part of Step S702 in exemplary embodiments of the present invention. For illustration purposes, Table 2 is referred to for a hypothetical series of transactions that could be minted in accordance with exemplary embodiments of the present invention:

TABLE 2

Example Illustrating Transactions Between Digital Wallets

| Time Stamp | Transferor Before Transaction | Transferee Before Transaction | Transaction Amount | Transferor After Transaction | Transferee After Transaction |
|---|---|---|---|---|---|
| 11:01:03 am | Wallet ABC123 Balance 125 | Wallet DEF456 Balance 25 | 35 | Wallet ABC123 Balance 90 | Wallet DEF456 Balance 60 |
| 11:01:35 am | Wallet XYZ123 Balance 300 | Wallet UVW456 Balance 20 | 70 | Wallet XYZ123 Balance 210 | Wallet UVW456 Balance 90 |
| 11:03:35 a.m. | Wallet GHI123 Balance 40 | Wallet JKL456 Balance 90 | 10 | Wallet GHI123 Balance 30 | Wallet JKL456 Balance 100 |
| 11:07:22 a.m. | Wallet MNO123 Balance 70 | Wallet PQR456 Balance 80 | 15 | Wallet MNO123 Balance 55 | Wallet PQR456 Balance 95 |
| 11:11:15 a.m. | Wallet AAA111 Balance 200 | Wallet ZZZ999 Balance 210 | 80 | Wallet AAA111 Balance 120 | Wallet ZZZ999 Balance 290 |

In Step S712, a minting software agent 114 receives transaction parameters for a pending digital asset transaction involving two or more digital asset addresses. Such transaction parameters may include digital asset amounts, and/or digital asset sending address and digital asset receiving addresses. In the example shown in Table 2, a first user using Digital Wallet ABC123 could transfer a sum of 35 of digital assets with a second user using Digital Wallet DEF456 during a first time period, such as 11:01:03 am referring to the above example. In such a case, the transaction parameters would be received by the minting software agent, such as: (i) Digital Wallet ABC123 identification and initial balance of 125; (ii) Digital Wallet DEF456 identification and initial balance of 25, which may be obtained from the public ledger; transaction amount of 35; (iii) timestamp of transaction at 11:01:03 am. The minting software agent may process the transaction to confirm it and may compute data such as (i) Digital Wallet ABC123 identification and end balance of 90; (ii) Digital Wallet DEF456 identification and end balance of 60. The minting software agent may generate and/or transmit process output indicators, such as an electronic indication of the transaction confirmation. These data may be written to a respective tamper-evident log along with a current time stamp associated with the log entry.

In Step S714 the minting software agent 114 records the transaction parameters in a respective tamper-evident log 412-1 stored in respective non-transitory computer-readable memory. Such transaction parameters may include digital asset amounts, and/or digital asset sending address and digital asset receiving addresses. Continuing the above example, the transaction parameters of the transaction at 11:01:35 am would be recorded in a tamper evident log: (i) Digital Wallet XYZ123 identification and initial balance of 300; (ii) Digital Wallet UVW456 identification and initial balance 20; transaction amount of 70; (iii) Digital Wallet XYZ123 identification and end balance of 210; (iv) Digital Wallet UVW456 identification and end balance of 90; (v) time stamp of transaction of 11:01:35 am. The minting software agent may generate and/or store process output indicators, such as an electronic indication of the transaction confirmation.

In Step S716 the minting software agent 114 verifies the pending digital asset transaction. For example, the minting software agents ensures the inputs equal or exceed the outputs and, verifies that the sending account has a sufficient balance to perform the transaction.

In Step S718 the minting software agent 114, records in the respective tamper-evident log 412-1 a first electronic indication of the transaction validity for the verified pending digital asset transaction. The electronic indication of transaction validity may identify a particular transaction and indicate that it has been confirmed by the minting agent.

In Step S720 the minting software agent 114 transmits, by, to one or more others of a plurality of super peer computing nodes, a second electronic indication of the transaction validity for the verified pending digital asset transaction, wherein the second electronic indication of the transaction validity providing a transaction settlement indication without waiting for a consensus, by nodes of the digital asset network, of accuracy of a distributed electronic public ledger 414. The second electronic indication may provide the same information as the first electronic indication, and the second electronic indication is transmitted to other nodes whereas the first electronic indication is stored in the log of the minting software agent.

In Step S722 the minting software agent 114 appends according to a periodic schedule, to a first instance of a distributed electronic public ledger 414 stored in the respective non-transitory computer-readable memory, a first electronic ledger portion comprising transaction details for the verified pending digital asset transaction along with respective transaction details for any other verified pending digital asset transactions not yet included in the first instance of the distributed electronic public ledger.

In Step S724 the minting software agent 114 transmits data comprising at least the first electronic ledger portion to the others of the plurality of super peer computing nodes 102-M.

In Step S726 the minting software agent 114 audits a respective tamper-evident log 140 of at least one software agent of one of the others of the plurality of super peer computing nodes 102-M. As discussed below with respect to FIG. 7D, a more detailed explanation of these processes in accordance with exemplary embodiments of the present invention is set forth.

FIG. 7C is a flow chart of exemplary non-minting operations of a super peer computing node in accordance with exemplary embodiments of the present invention. Such minting operations may be performed as part of Step S704 in exemplary embodiments of the present invention.

In Step S732, a non-minting software agent 428 (e.g., running on one of a plurality of super peer computing nodes)

receives transaction parameters for a pending digital asset transaction. Such transaction parameters may include digital asset amounts, and/or digital asset sending address and digital asset receiving addresses.

In Step S734 the non-minting software agent 428 records the transaction parameters in a respective tamper-evident log 412-2 stored in respective non-transitory computer-readable memory. Such transaction parameters may include digital asset amounts, and/or digital asset sending address and digital asset receiving addresses.

In Step S736 the non-minting software 428 agent receives from a minting software agent 426, an electronic indication of transaction validity for the pending digital asset transaction.

In Step S738 the non-minting software agent 428 records the electronic indication of transaction validity for the pending digital asset transaction in the respective tamper-evident log 412-2.

In Step S740 the non-minting software agent 428 relays to one or more gateway nodes 108-P, the electronic indication of transaction validity for the pending digital asset transaction to be delivered at least to respective user devices associated with the pending digital asset transaction.

In Step S742 the non-minting software agent 428 accesses a second tamper-evident log 412-2 of at least one software agent of another super peer computing node.

In Step S744 the non-minting software agent 428 audits the second tamper-evident log 412-2.

In Step S746 the non-minting software agent 428 computes, a respective independent instance of a first electronic ledger portion of a distributed electronic public ledger.

In Step S748 the non-minting software agent may receive from the minting software agent, data comprising at least a first master electronic ledger portion of the distributed electronic public ledger, whereas the master copy is generated by the current minting software agent.

In Step S750 the non-minting software agent 428 compares the respective independent instance of the first electronic ledger portion with the received data comprising at least the first master electronic ledger portion.

Figure 7D:
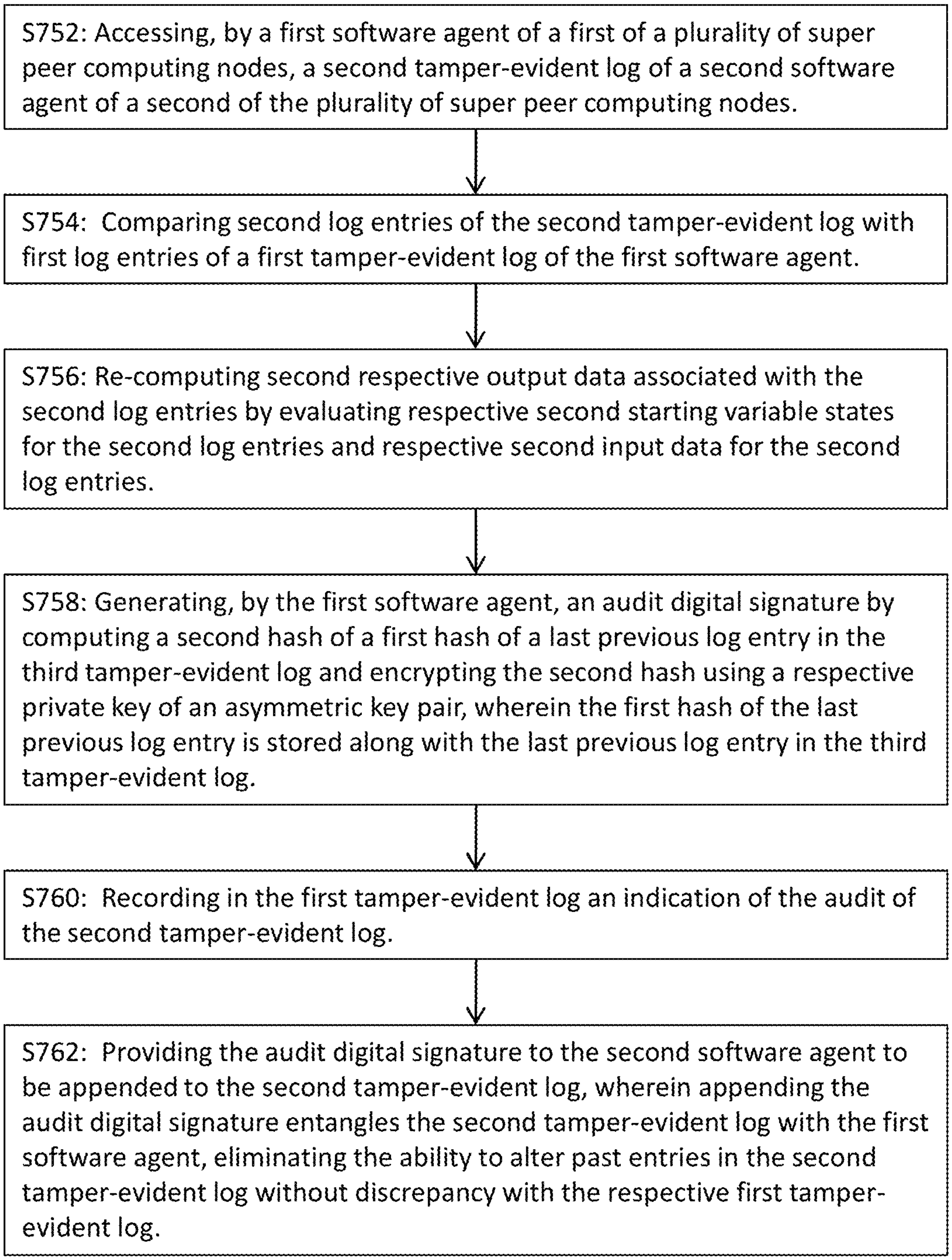
FIG. 7D is a flow chart of auditing a tamper-evident log in accordance with exemplary embodiments of the present invention.

FIG. 7D is a flow chart of auditing a tamper-evident log in accordance with exemplary embodiments of the present invention. A sufficient record may be stored in the log of a first agent such that a second peer agent can replay the log of the first agent to verify as correct the behavior of the first agent. In embodiments, the minting agent may audit its neighbors by analyzing their respective tamper-evident logs. When a minting agent audits its peer non-minting agents, it can validate their correct behavior, which may have the indirect effect of verifying the mint agent. For example, when the minting agent transmits a new block, it can then check that each non-minting super peer received the block it sent and that it is not corrupted. In embodiments, non-minting agents can also audit logs of their neighboring agents.

An audit verification method of the second peer agent uses the obtained starting context and inputs to replay a particular action (from among the possible actions of the audited agent) and compare the recomputed ending state variable values and compare the recomputed sent message (s), to the obtained ending context and outputs from the audited agent's log. If corresponding values are equal within the scope of the simulation, e.g. ignoring real clock time, then the examined peer may be deemed to have behaved correctly.

In Step S752 a first software agent (which can be a minting agent or a non-minting agent) accesses a first of a plurality of super peer computing nodes 102, a second tamper-evident log 412-2 of a second software agent of a second of the plurality of super peer computing nodes.

In Step S754: The first software agent may compare second log entries of the second tamper-evident log 412-2 with first log entries of a first tamper-evident log 412-1 of the first software agent 426.

In Step S756: The first software agent may re-compute second respective output data associated with the second log entries by evaluating respective second starting variable states for the second log entries and respective second input data for the second log entries.

In Step S758 the first software agent 426 generates an audit digital signature by computing a second hash of a first hash of a last previous log entry in the third tamper-evident log and encrypting the second hash using a respective private key of an asymmetric key pair, wherein the first hash of the last previous log entry is stored along with the last previous log entry in the third tamper-evident log 412-3.

In Step S760, an indication of the audit of the second tamper-evident log 412-2 may be recorded in the first tamper-evident log 412-1.

In Step S762, the second software agent 428 may be provided to be appended to the second tamper-evident log 412-2, wherein appending the audit digital signature entangles the second tamper-evident log with the first software agent, eliminating the ability to alter past entries in the second tamper-evident log without discrepancy with the respective first tamper-evident log.

FIG. 8 is a schematic diagram of minting role scheduling in accordance with exemplary embodiments of the present invention. It illustrates that at any given time T only one super peer 802 is scheduled to run a minting agent 804. The other super peers run non-minting agents 806 during that time, which perform digital asset network operations, such as verifying each other's logs and/or verifying the ledger updates performed by the minting agent 804.

In embodiments, a digital asset system is disclosed. The digital asset system may comprise a plurality of super peer computing nodes operating in a cooperative computing architecture to facilitate provision of a digital asset network using proof of work, each node comprising respective one or more processors and respective non-transitory computer-readable memory and configured to run on its respective one or more processors one or more software agents to administer the digital asset network.

The digital asset system further may comprise an administrative super peer computing node running a configuration software agent that schedules computing roles for the plurality of super peer computing nodes, wherein the configuration software agent schedules for a first period of time a first one of the plurality of super peer computing nodes to run a first minting software agent configured to perform respective minting agent operations such as those set forth in FIG. 7B.

In Step 712, the minting agent operation comprises receiving transaction parameters for a pending digital asset transaction involving two or more digital asset addresses, the transaction parameters comprising one or more digital asset transaction inputs each comprising an input amount and a respective digital signature and associated with a sending digital asset address, and the transaction parameters further comprising at least one digital asset transaction output associated with a receiving digital asset address.

In Step 714, the minting agent operation comprises recording the transaction parameters in a first tamper-evident log stored in first non-transitory computer-readable memory. In embodiments, each entry in the first tamper-evident log may comprises (1) respective first log entry data comprising at least the transaction data and a first timestamp and (2) a respective first hash of the respective first log entry data.

In Step 716, the minting agent operation comprises verifying the pending digital asset transaction at least by evaluating the respective digital signature associated with each digital asset transaction input to confirm the digital asset transaction input is an authorized input and previously unspent and by confirming that the sum of the authorized inputs equals or exceeds the digital asset transaction output.

In Step 718, the minting agent operation comprises recording in the first tamper-evident log a first electronic indication of the transaction validity for the verified pending digital asset transaction.

In Step 720, the minting agent operation comprises transmitting, to one or more others of the plurality of super peer computing nodes, a second electronic indication of the transaction validity for the verified pending digital asset transaction, the second electronic indication of the transaction validity providing a transaction settlement indication without waiting for a consensus, by nodes of the digital asset network, of accuracy of a distributed electronic public ledger.

In Step 722, the minting agent operation comprising appending, according to a periodic schedule, to a first instance of a distributed electronic public ledger stored in the first non-transitory computer-readable memory a first electronic ledger portion comprising transaction details for the verified pending digital asset transaction along with respective transaction details for any other verified pending digital asset transactions not yet included in the first instance of the distributed electronic public ledger. In embodiments, the first instance of the distributed electronic public ledger may be stored in different non-transitory computer-readable memory.

In Step 724, the minting agent operation comprises transmitting data comprising at least the first electronic ledger portion to the others of the plurality of super peer computing nodes.

In Step 726, the minting agent operation comprises auditing a respective tamper-evident log of at least one software agent of one of the others of the plurality of super peer computing nodes.

In embodiments, the configuration software agent may schedule for the first period of time the others of the plurality of super peer computing nodes to run respective non-minting software agents wherein at least some of the non-minting software agents are configured to perform the steps as outlined in FIG. 7C.

In Step 732, the non-minting software agents receive the transaction parameters for the pending digital asset transaction.

In Step 734, the non-minting software agent records the transaction parameters in a respective second tamper-evident log stored in respective non-transitory computer-readable memory.

In Step 736, the non-minting software agent receives, from the first minting software agent, the second electronic indication of the transaction validity for the verified pending digital asset transaction.

In Step 738, the non-minting software agent records the second electronic indication of the transaction validity for the verified pending digital asset transaction in the respective second tamper-evident log.

In embodiments, the non-minting software agent may further access respective third tamper-evident logs of at least some of the plurality of super peer computing nodes to verify entries in the respective second tamper-evident log. For example, a particular non-minting agent can record in its own log a messages that it sends to one or more other super peer nodes. Then, that agent can check each recipient super peer node to verify that each message was received and not corrupted.

In embodiments, the non-minting software agent may further relay to one or more gateway nodes the second electronic indication of the transaction validity for the verified pending digital asset transaction to be delivered at least to respective user devices associated with the two or more digital asset addresses.

In embodiments, the non-minting software agent may further compute a respective independent instance of the first electronic ledger portion.

In embodiments, the non-minting software agent may further receiving, from the first minting software agent, data comprising at least the first electronic ledger portion.

In embodiments, the non-minting software agent may further compare the respective independent instance of the first electronic ledger portion with the received data comprising at least the first electronic ledger portion. In embodiments, the system may generate, transmit, and/or display an error message if not the ledger portions are not equal, such as if they do not compute to the same hash values.

In embodiments, the configuration software agent schedules for a second period of time a second one of the plurality of super peer computing nodes to run a second minting software agent to perform respective minting agent operations.

In embodiments, the configuration software agent schedules computing roles for the plurality of super peer computing nodes according to a predefined schedule stored in respective non-transitory computer-readable memory operatively connected to the administrative super peer computing node and accessible by the configuration software agent.

In embodiments, the predefined schedule may identify for each of a plurality of periods of time (e.g., comprising a daily schedule) one minting agent to be run on a respective one of the plurality of super peer computing nodes according to times when trading markets are active in a respective geographic location of the respective one of the plurality of super peer computing nodes.

In embodiments, the configuration software agent schedules computing roles for the plurality of super peer computing nodes based at least in part upon any of respective available processing power of at least one of the plurality of super peer computing nodes, respective available transmission bandwidth of at least one of the plurality of super peer computing nodes, respective ownership or control of at least one of the plurality of super peer computing nodes, or geographic location of at least one of the plurality of super peer computing nodes.

In embodiments, the first electronic ledger portion may be appended to the first instance of the distributed electronic public ledger comprises creation of a predefined amount of digital assets. In embodiments, the predefined amount may be changed over time, e.g., according to a schedule or by reprogramming.

In embodiments, the periodic schedule comprises a predefined frequency with which to append new electronic ledger portions to the first instance of the distributed electronic public ledger. In embodiments, the predefined frequency may be 30 seconds, 1 minute, 10 minutes, 1 hour, 1 day, to name a few.

In embodiments, the periodic schedule comprises one or more predefined times at which to append new electronic ledger portions to the first instance of the distributed electronic public ledger. In embodiments, the one or more predefined times may correspond to a market opening time and/or a market closing time. In embodiments, the predefined time may be any of 12 AM E.T., 9 AM E.T., and/or 5 PM E.T., to name a few.

In embodiments, the at least some of the non-minting software agents are further configured to perform the steps as follows. The non-minting agent may audit a third tamper-evident log of a third one of the others of the plurality of super peer computing nodes running a non-minting software agent by. The non-minting agent may access a third tamper-evident log of the third one of the others of the plurality of super peer computing nodes. The non-minting agent may compare respective log entries of the third tamper-evident log with log entries of the respective second tamper-evident log. The non-minting agent may generate an audit digital signature by computing a second hash of a last previous log entry in the third tamper-evident log and encrypting the second hash using a respective private key of an asymmetric key pair. The non-minting agent may recording in the respective second tamper-evident log an indication of the audit of the third tamper-evident log. The non-minting agent may provide the audit digital signature to the third one of the others of the plurality of super peer computing nodes to be appended to the third tamper-evident log, wherein appending the audit digital signature entangles the third tamper-evident log with the respective software agent that provided the audit digital signature, eliminating the ability to alter past entries in the third tamper-evident log without discrepancy with the respective second tamper-evident log.

In embodiments, the computing by each of the at least some of the non-minting software agents, the respective independent instance of the first electronic ledger portion comprises the following steps. The at least some non-minting software agents accessing transaction parameters for a plurality of digital asset transactions from the respective second tamper-evident log of the respective non-minting software agent. The at least some non-minting agents determining a subset of the plurality of digital asset transactions that are unverified pending digital asset transactions for which respective indications of respective transaction validity have not been received from the first minting software agent. The at least some non-minting agents computing the respective independent instance of the first electronic ledger portion according to a programmed minting process.

In embodiments, during the second period of time the configuration software agent schedules the first one of the plurality of super peer computing nodes to run a respective non-minting software agent.

In embodiments, the system further comprises archiving nodes each comprising one or more respective processors and respective non-transitory computer-readable memory and configured perform the steps of: storing in the respective non-transitory computer-readable memory a respective instance of the distributed electronic public ledger; receiving data comprising at least the first electronic ledger portion; appending the first electronic ledger portion to the respective instance of the distributed electronic public ledger to generate a respective updated instance of the distributed electronic public ledger; and storing the respective updated instance of the distributed electronic public ledger.

In embodiments, a digital asset system is disclosed. The digital asset system comprise a plurality of super peer computing nodes operating in a cooperative computing architecture to facilitate provision of a digital asset network using proof of work, each node comprising respective one or more processors and respective non-transitory computer-readable memory and configured to run on its respective one or more processors one or more software agents to administer the digital asset network.

The digital asset system further comprises an administrative super peer computing node running a configuration software agent that schedules computing roles for the plurality of super peer computing nodes.

A first one of the plurality of super peer computing nodes running a first minting software agent during a first period of time according to scheduling instructions received from the configuration software agent, wherein the first minting software agent is configured to perform the steps of: receiving transaction parameters for a pending digital asset transaction involving two or more digital asset addresses, the transaction parameters comprising one or more digital asset transaction inputs each comprising an input amount, a respective digital signature, and associated with a sending digital asset address, and the transaction parameters further comprising at least one digital asset transaction output associated with a receiving digital asset address; recording the transaction parameters in a first tamper-evident log stored in first non-transitory computer-readable memory, wherein each entry in the first tamper-evident log comprises a respective first hash of respective first log entry data comprising at least the transaction data, a first timestamp, and a hash of the respective previous log entry, which first hash is digitally signed using a first private key of an asymmetric key pair associated with the first minting software agent; verifying the pending digital asset transaction at least by evaluating the respective digital signature associated with each digital asset transaction input to confirm the digital asset transaction input is an authorized input and previously unspent and by confirming that the sum of the authorized inputs equals or exceeds the digital asset transaction output; recording in the first tamper-evident log a first electronic indication of the transaction validity for the verified pending digital asset transaction; transmitting, to one or more others of the plurality of super peer computing nodes, a second electronic indication of the transaction validity for the verified pending digital asset transaction, the second electronic indication of the transaction validity providing a transaction settlement indication without waiting for updates to a distributed electronic public ledger; appending, according to a periodic schedule, to a first instance of a distributed electronic public ledger stored in the first non-transitory computer-readable memory a first electronic ledger portion comprising transaction details for the verified pending digital asset transaction along with respective transaction details for any other verified pending digital asset transactions not yet included in the first instance of the distributed electronic public ledger; transmitting data comprising at least the first electronic ledger portion to the others of the plurality of super peer computing nodes; and accessing respective tamper-evident logs of at least one of the others of the plurality of super peer computing nodes, used to verify entries in the first tamper-evident log.

The system further receives, from the configuration software agent, instructions to cease running the first minting software agent during a second period of time and to run a non-minting software agent during the second period of time configured to perform the steps of: receiving second transaction parameters for a second pending digital asset transaction; recording the second transaction parameters in a second tamper-evident log stored in respective non-transitory computer-readable memory; receiving, from a second one of the plurality of super peer computing nodes running a second minting software agent during the second period of time, an electronic indication of transaction validity associated with the second pending digital asset transaction; recording the electronic indication of transaction validity for the second pending digital asset transaction in the second tamper-evident log; accessing tamper-evident logs of at least some of the plurality of super peer computing nodes used to verify entries in the second tamper-evident log; relaying to one or more gateway nodes the electronic indication of transaction validity for the second pending digital asset transaction to be delivered at least to respective user devices associated with the second pending digital asset transaction; computing a respective independent instance of a second electronic ledger portion; receiving from the second one of the plurality of super peer computing nodes data comprising at least a minting second electronic ledger portion; and comparing the respective independent instance of the second electronic ledger portion with the received data comprising at least the minting second electronic ledger portion.

In embodiments, the configuration software agent schedules computing roles for the plurality of super peer computing nodes according to a predefined schedule stored in respective non-transitory computer-readable memory operatively connected to the administrative super peer computing node and accessible by the configuration software agent.

In embodiments, the configuration software agent schedules computing roles for the plurality of super peer computing nodes based at least in part upon any of respective available processing power of at least one of the plurality of super peer computing nodes, respective available transmission bandwidth of at least one of the plurality of super peer computing nodes, respective ownership or control of at least one of the plurality of super peer computing nodes, or geographic location of at least one of the plurality of super peer computing nodes.

In embodiments, the first electronic ledger portion is appended to the first instance of the distributed electronic public ledger comprises creation of a predefined amount of digital assets.

In embodiments, the periodic schedule comprises a predefined frequency with which to append new electronic ledger portions to the first instance of the distributed electronic public ledger.

In embodiments, the periodic schedule comprises one or more predefined times at which to append new electronic ledger portions to the first instance of the distributed electronic public ledger.

FIGS. 9A-F are schematic unified modeling language (UML) diagrams of operations in a digital asset network in accordance with exemplary embodiments of the present invention.

Figure 9A:
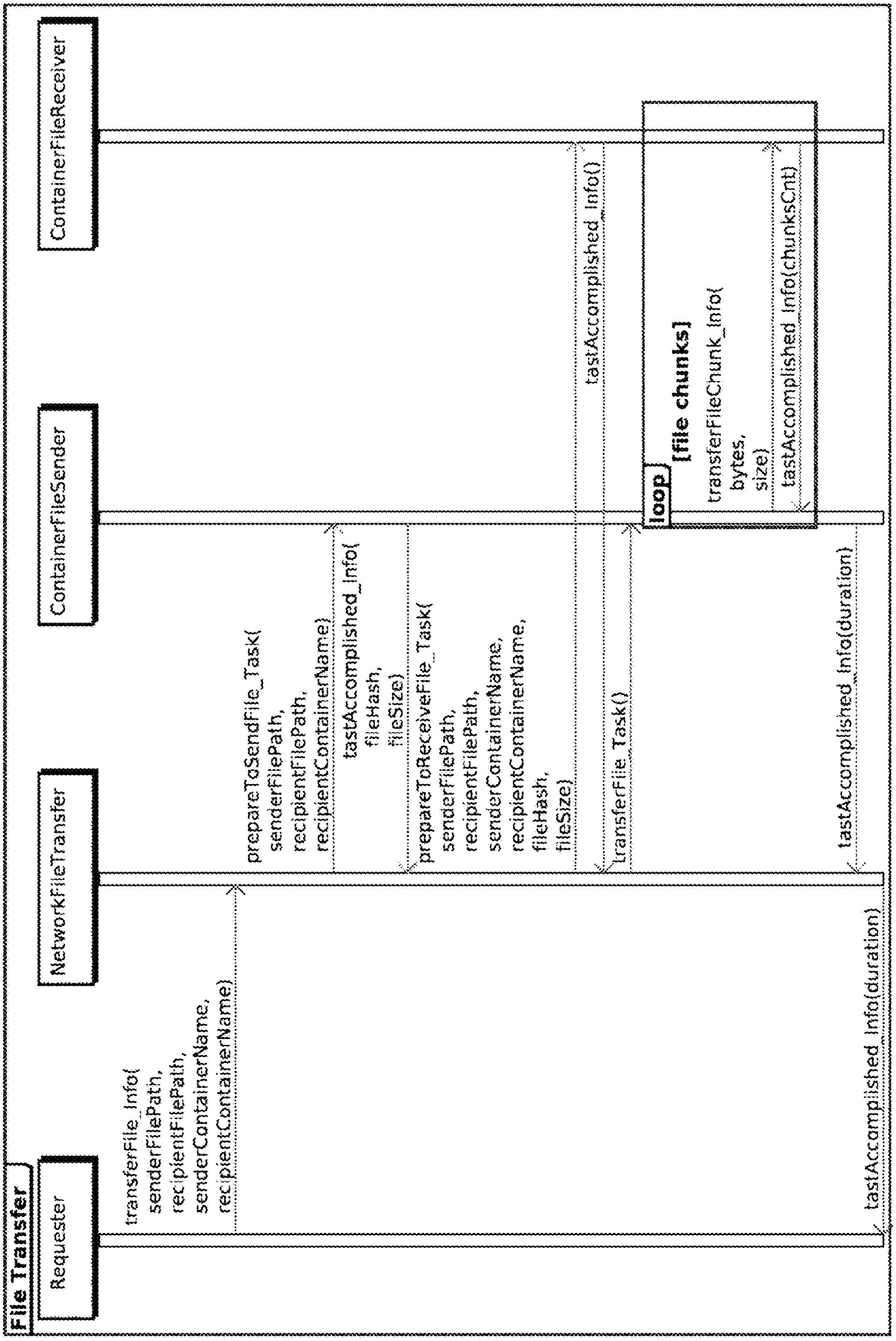
FIGS. 9A-F are schematic diagrams of operations in a digital asset network in accordance with exemplary embodiments of the present invention.

FIG. 9A is a UML sequence diagram showing message flow corresponding to a file transfer between a sending and a receiving software agent. Time flows from top to bottom on the chart. Directed arrows indicate particular messages in the conversation required to request and to execute a file transfer. The Requester agent may request the transfer, and the Network File Transfer agent may coordinate the transfer. The Container File Sender agent may send the requested file upon command, and the Container File Receiver agent may receive and verify the transferred file, chunk by chunk.

Figure 9C:
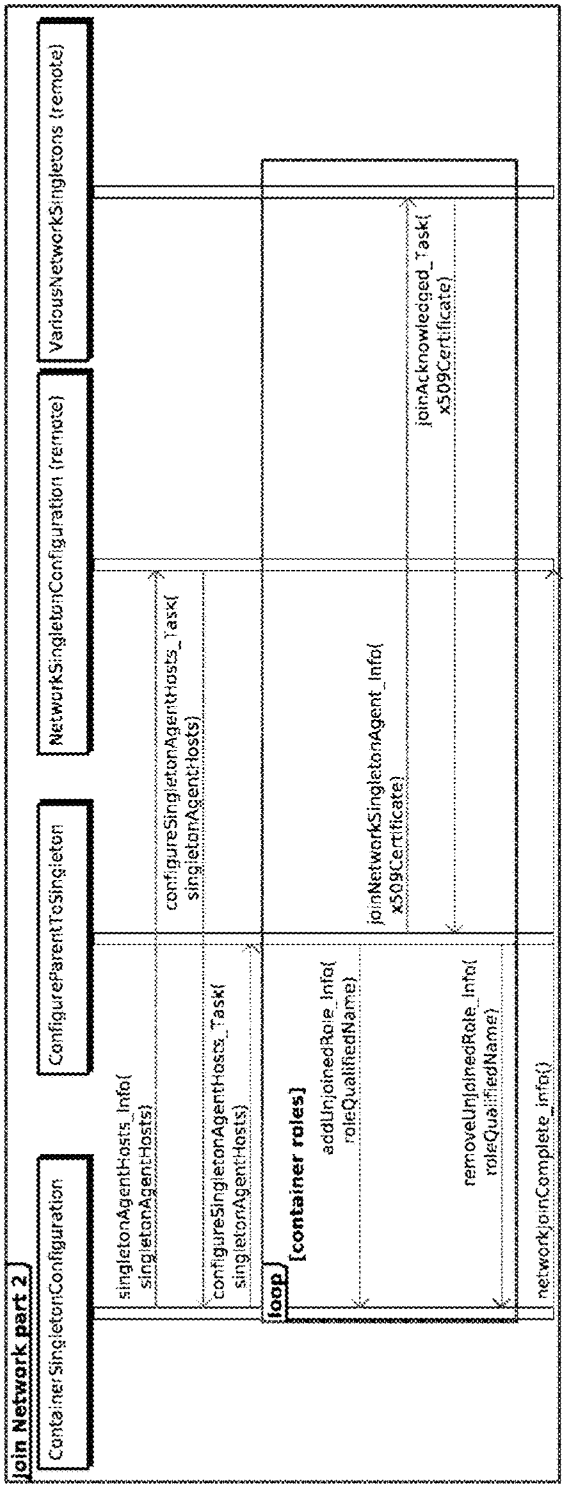
Figure 9B:
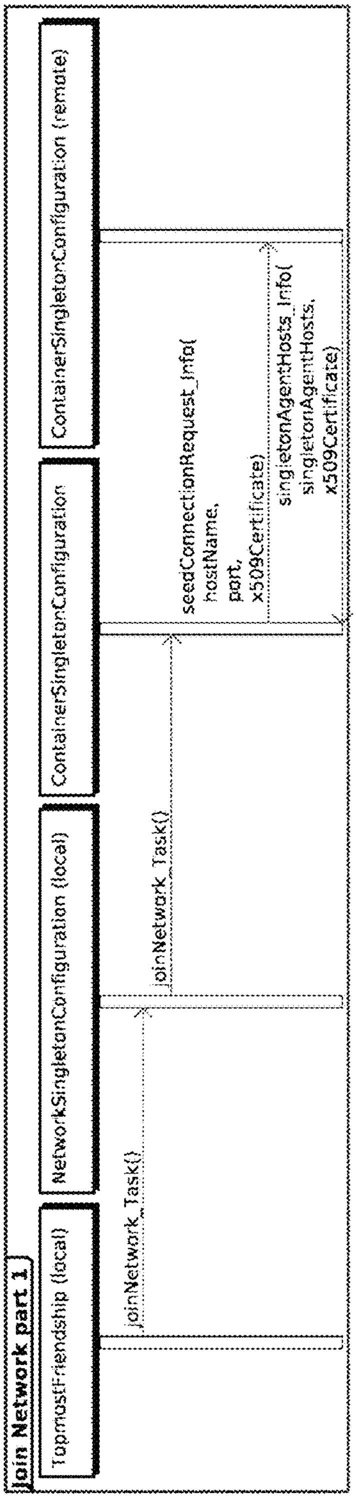

FIG. 9B is a UML sequence diagram showing the first part of how a new super peer requests connection to the agent network. FIG. 9C is a UML sequence diagram showing the second part of how a new super peer connects to the agent network. Each agent in the joining node connects to the unique superior super peer agent in the network.

Figure 9E:
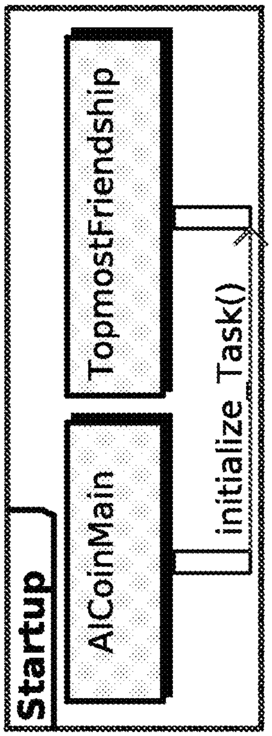
Figure 9D:
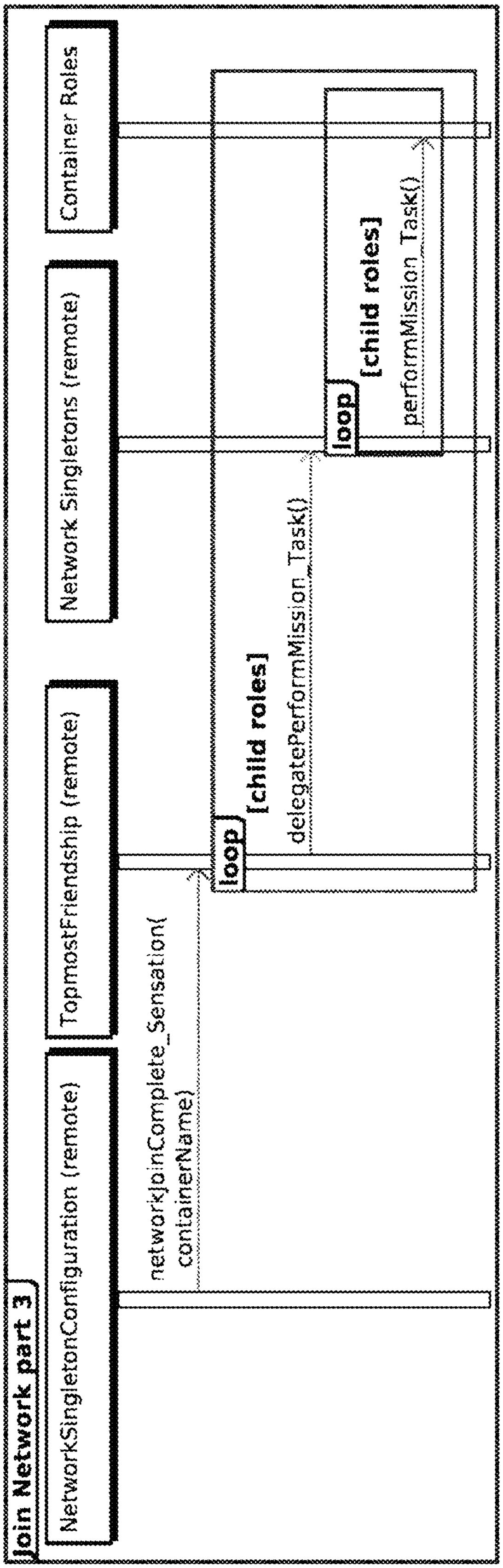

FIG. 9D is a UML sequence diagram showing the third part of how a new super peer connects to the agent network. When each agent in the joining node connects to its superior agent, then the network configuration agent may issue a cascade of messages that can cause each agent in the joining peer to initialize and to begin performing their respective missions.

FIG. 9E is a UML sequence diagram showing the initialization of a peer via a message sent at startup to the topmost agent, sometimes referred to as the friendship agent, which is the superior agent in the hierarchical control network.

Figure 9F:
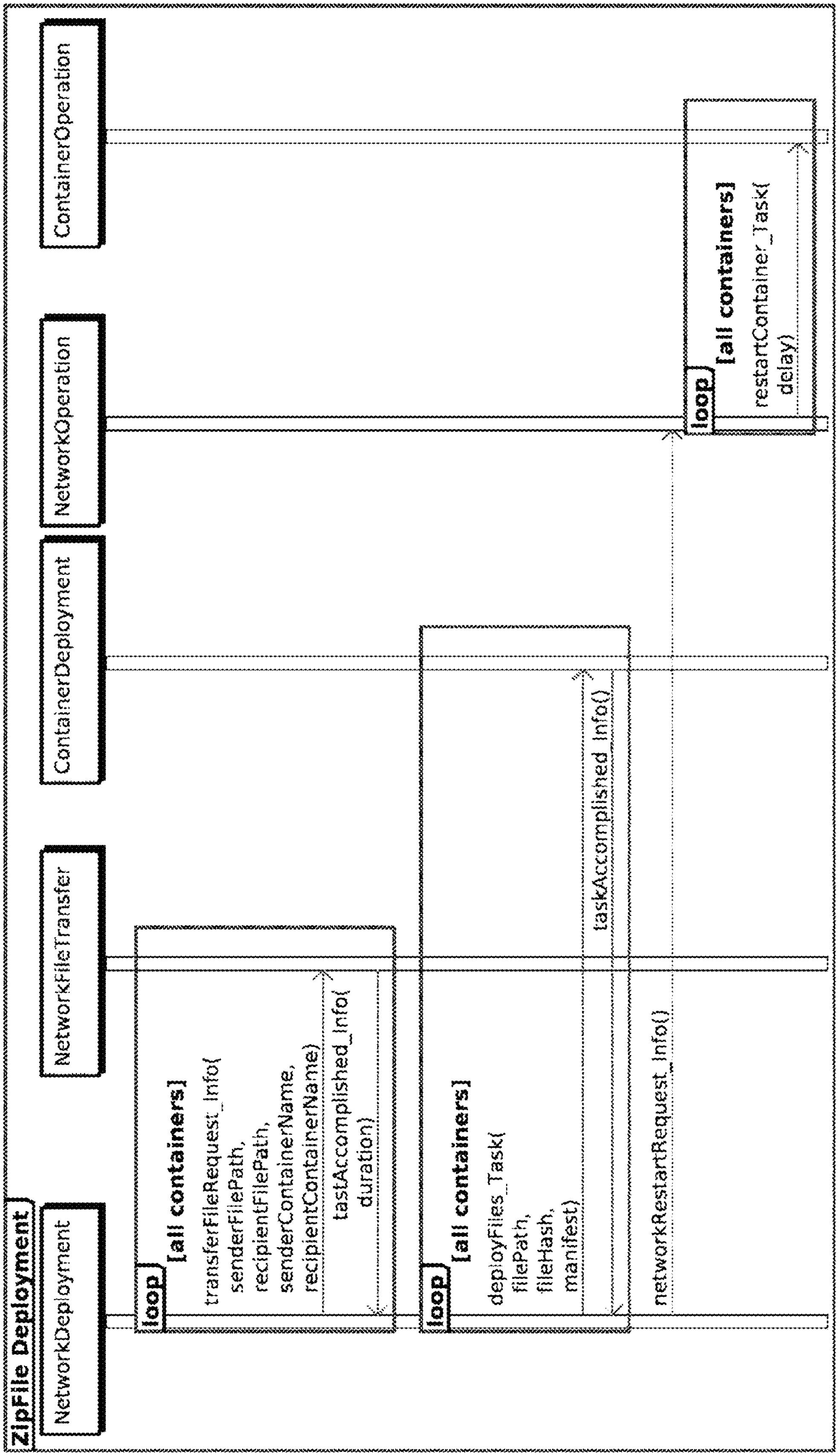

FIG. 9F is a UML sequence diagram showing the network deployment of a new software version, which in the exemplary embodiment is packaged as a zip archive file. The File Transfer process as described in FIG. 9A can be used to copy the new zip file to each of the remote nodes. When the deployment is completed, the network operations agent can restart each node in the network.

The Appendix provides excerpts of exemplary software that enable creation and/or implementation of an exemplary version of the cooperative super peer digital asset network of the present invention. The exemplary software agents are named according to the convention <container>.<agent>.<role>, where the container is the name of the peer, the agent has a particular mission, and the agent consists of roles, which provide the skills that fulfill the agent's mission.

Section I of the Appendix provides a list of the singleton agents, which can be active only on one peer at a time. Indented for each role of the singleton agent are the directly subordinate roles which may be on the self peer or any other peer in the network.

Section II of the Appendix includes a filtered version of Section I, in which only non-singleton child nodes are displayed.

Section III of the Appendix provides a list of the agents which make up a particular peer, i.e. TestContainer. Indented for each role of an agent are the directly subordinate roles which may be on the self peer or any other peer in the network.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. A digital asset system comprising:

a plurality of super peer computing nodes operating in a cooperative computing architecture to facilitate provision of a digital asset network using proof of work, each node comprising respective one or more processors and respective non-transitory computer-readable memory and configured to run on its respective one or more processors one or more software agents to administer the digital asset network, at least some of the plurality of super peer computing nodes arranged in a concentric ring architecture comprising at least one inner concentric ring of super peer computing nodes and at least one outer concentric ring of super peer computing nodes, wherein each super peer computing node within the at least one inner concentric ring is operatively connected to at least one other super peer computing node within the at least one inner concentric ring, wherein each super peer computing node within the at least one outer concentric ring is operatively connected to at least one other super peer computing node within the at least one outer concentric ring, and wherein at least one super peer computing node in the at least one inner concentric ring is operatively connected to at least one super peer computing node in the at least one outer concentric ring;

an administrative super peer computing node running a configuration software agent that schedules computing roles for the plurality of super peer computing nodes, (a) wherein the configuration software agent schedules, for a first period of time, a first one of the super peer computing nodes within the at least one outer concentric ring of super peer computing nodes to run a first minting software agent configured to perform respective minting agent operations comprising:

(i) receiving transaction parameters for a pending digital asset transaction involving two or more digital asset addresses, the transaction parameters comprising one or more digital asset transaction inputs each comprising an input amount and a respective digital signature and associated with a sending digital asset address, and the transaction parameters further comprising at least one digital asset transaction output associated with a receiving digital asset address;

(ii) recording the transaction parameters in a first tamper-evident log stored in first non-transitory computer-readable memory, wherein each entry in the first tamper-evident log comprises (1) respective first log entry data comprising at least the transaction data and a first timestamp and (2) a respective first hash of the respective first log entry data;

(iii) verifying the pending digital asset transaction at least by evaluating the respective digital signature associated with each digital asset transaction input to confirm that the digital asset transaction input is an authorized input and previously unspent and by confirming that the sum of the authorized inputs equals or exceeds the digital asset transaction output;

(iv) recording in the first tamper-evident log a first electronic indication of transaction validity for the verified pending digital asset transaction;

(v) transmitting, to one or more others of the plurality of super peer computing nodes, a second electronic indication of the transaction validity for the verified pending digital asset transaction, the second electronic indication of the transaction validity providing a transaction settlement indication without waiting for a consensus, by nodes of the digital asset network, of accuracy of a distributed electronic public ledger, wherein at least one of the one or more others of the plurality of super peer computing nodes are within the at least one inner concentric ring of super peer computing nodes;

(vi) appending, according to a periodic schedule, to a first instance of a distributed electronic public ledger stored in the first non-transitory computer-readable memory a first electronic ledger portion comprising transaction details for the verified pending digital asset transaction along with respective transaction details for any other verified pending digital asset transactions not yet included in the first instance of the distributed electronic public ledger to generate an updated distributed electronic public ledger to be stored in the first non-transitory computer-readable memory;

(vii) transmitting data comprising at least the first electronic ledger portion to the others of the plurality of super peer computing nodes to update the distributed electronic ledger at the others of the plurality of super peer computing nodes; and (viii) auditing a respective tamper-evident log of at least one software agent of one of the others of the plurality of super peer computing nodes;

(b) wherein the configuration software agent schedules for the first period of time the others of the plurality of super peer computing nodes to run respective non-minting software agents wherein at least some of the non-minting software agents are configured to perform the steps of:

(i) receiving the transaction parameters for the pending digital asset transaction;

(ii) recording the transaction parameters in a respective second tamper-evident log stored in respective non-transitory computer-readable memory;

(iii) receiving, from the first minting software agent, the second electronic indication of the transaction validity for the verified pending digital asset transaction;

(iv) recording the second electronic indication of the transaction validity for the verified pending digital asset transaction in the respective second tamper-evident log;

(v) accessing respective third tamper-evident logs of at least some of the plurality of super peer computing nodes to verify entries in the respective second tamper-evident log;

(vi) relaying to one or more gateway nodes the second electronic indication of the transaction validity for the verified pending digital asset transaction to be delivered at least to respective user devices associated with the two or more digital asset addresses;

(vii) computing a respective independent instance of the first electronic ledger portion;

(viii) receiving, from the first minting software agent, data comprising at least the first electronic ledger portion; and (ix) comparing the respective independent instance of the first electronic ledger portion with the received data comprising at least the first electronic ledger portion;

wherein the configuration software agent schedules for a second period of time one of the others of the plurality of super peer computing nodes to run a second minting software agent to perform respective minting agent operations, wherein during the second period of time the configuration software agent schedules the first one of the plurality of super peer computing nodes to run a respective non-minting software agent, and wherein the periodic schedule comprises a predefined frequency with which to append new electronic ledger portions to the first instance of the distributed electronic public ledger.

2. The system of claim 1, wherein the configuration software agent schedules computing roles for the plurality of super peer computing nodes according to a predefined schedule stored in respective non-transitory computer-readable memory operatively connected to the administrative super peer computing node and accessible by the configuration software agent.

3. The system of claim 1, wherein the configuration software agent schedules computing roles for the plurality of super peer computing nodes based at least in part upon any of respective available processing power of at least one of the plurality of super peer computing nodes, respective available transmission bandwidth of at least one of the plurality of super peer computing nodes, respective ownership or control of at least one of the plurality of super peer computing nodes, or geographic location of at least one of the plurality of super peer computing nodes.

4. The system of claim 1, wherein appending the first electronic ledger portion to the first instance of the distributed electronic public ledger comprises creation of a predefined amount of digital assets.

5. The system of claim 1, wherein the periodic schedule comprises one or more predefined times at which to append new electronic ledger portions to the first instance of the distributed electronic public ledger.

6. The system of claim 1, wherein the at least some of the non-minting software agents are further configured to perform the steps of:

(x) auditing a third tamper-evident log of a third one of the others of the plurality of super peer computing nodes running a non-minting software agent by:

(1) accessing a third tamper-evident log of the third one of the others of the plurality of super peer computing nodes;

(2) comparing respective log entries of the third tamper-evident log with log entries of the respective second tamper-evident log;

(3) generating an audit digital signature by computing a second hash of a last previous log entry in the third tamper-evident log and encrypting the second hash using a respective private key of an asymmetric key pair;

(4) recording in the respective second tamper-evident log an indication of the audit of the third tamper-evident log; and (5) providing the audit digital signature to the third one of the others of the plurality of super peer computing nodes to be appended to the third tamper-evident log, wherein appending the audit digital signature entangles the third tamper-evident log with the respective software agent that provided the audit digital signature, eliminating the ability to alter past entries in the third tamper-evident log without discrepancy with the respective second tamper-evident log.

7. The system of claim 1, wherein computing by each of the at least some of the non-minting software agents, the respective independent instance of the first electronic ledger portion comprises:

(1) accessing transaction parameters for a plurality of digital asset transactions from the respective second tamper-evident log of the respective non-minting software agent;

(2) determining a subset of the plurality of digital asset transactions that are unverified pending digital asset transactions for which respective indications of respective transaction validity have not been received from the first minting software agent;

(3) computing the respective independent instance of the first electronic ledger portion according to a programmed minting process.

8. The system of claim 1, further comprising archiving nodes each comprising one or more respective processors and respective non-transitory computer-readable memory and configured to perform the steps of:

storing in the respective non-transitory computer-readable memory a respective instance of the distributed electronic public ledger;

receiving data comprising at least the first electronic ledger portion;

appending the first electronic ledger portion to the respective instance of the distributed electronic public ledger to generate a respective updated instance of the distributed electronic public ledger; and storing the respective updated instance of the distributed electronic public ledger.

9. A digital asset system comprising:

(a) a plurality of super peer computing nodes operating in a cooperative computing architecture to facilitate provision of a digital asset network using proof of work, each node comprising respective one or more processors and respective non-transitory computer-readable memory and configured to run on its respective one or more processors one or more software agents to administer the digital asset network, at least some of the plurality of super peer computing nodes arranged in a concentric ring architecture comprising at least one inner concentric ring of super peer computing nodes and at least one outer concentric ring of super peer computing nodes, wherein each super peer computing node within the at least one inner concentric ring is operatively connected to at least one other super peer computing node within the at least one inner concentric ring, wherein each super peer computing node within the at least one outer concentric ring is operatively connected to at least one other super peer computing node within the at least one outer concentric ring, and wherein at least one super peer computing node in the at least one inner concentric ring is operatively connected to at least one super peer computing node in the at least one outer concentric ring;

(b) an administrative super peer computing node running a configuration software agent that schedules computing roles for the plurality of super peer computing nodes;

(c) a first one of the super peer computing nodes within the at least one outer concentric ring of super peer computing nodes running a first minting software agent during a first period of time according to scheduling instructions received from the configuration software agent, wherein the first minting software agent is configured to perform the steps of:

(i) receiving transaction parameters for a pending digital asset transaction involving two or more digital asset addresses, the transaction parameters comprising one or more digital asset transaction inputs each comprising an input amount, a respective digital signature, and associated with a sending digital asset address, and the transaction parameters further comprising at least one digital asset transaction output associated with a receiving digital asset address;

(ii) recording the transaction parameters in a first tamper-evident log stored in first non-transitory computer-readable memory, wherein each entry in the first tamper-evident log comprises a respective first hash of respective first log entry data comprising at least the transaction data, a first timestamp, and a hash of the respective previous log entry, which first hash is digitally signed using a first private key of an asymmetric key pair associated with the first minting software agent;

(iii) verifying the pending digital asset transaction at least by evaluating the respective digital signature associated with each digital asset transaction input to confirm that the digital asset transaction input is an authorized input and previously unspent and by confirming that the sum of the authorized inputs equals or exceeds the digital asset transaction output;

(iv) recording in the first tamper-evident log a first electronic indication of transaction validity for the verified pending digital asset transaction;

(v) transmitting, to one or more others of the plurality of super peer computing nodes, a second electronic indication of the transaction validity for the verified pending digital asset transaction, the second electronic indication of the transaction validity providing a transaction settlement indication without waiting for updates to a distributed electronic public ledger, wherein at least one of the one or more others of the plurality of super peer computing nodes are within the at least one inner concentric ring of super peer computing nodes;

(vi) appending, according to a periodic schedule, to a first instance of a distributed electronic public ledger stored in the first non-transitory computer-readable memory a first electronic ledger portion comprising transaction details for the verified pending digital asset transaction along with respective transaction details for any other verified pending digital asset transactions not yet included in the first instance of the distributed electronic public ledger to generate an updated distributed electronic public ledger to be stored in the first non-transitory computer-readable memory;

(vii) transmitting data comprising at least the first electronic ledger portion to the others of the plurality of super peer computing nodes to update the distributed electronic ledger at the others of the plurality of super peer computing nodes; and (viii) accessing respective tamper-evident logs of at least one of the others of the plurality of super peer computing nodes, used to verify entries in the first tamper-evident log;

(ix) receiving, from the configuration software agent, instructions to cease running the first minting software agent during a second period of time and to run a non-minting software agent during the second period of time configured to perform the steps of:

(1) receiving second transaction parameters for a second pending digital asset transaction;

(2) recording the second transaction parameters in a second tamper-evident log stored in respective non-transitory computer-readable memory;

(3) receiving, from one of the others of the plurality of super peer computing nodes running a second minting software agent during the second period of time, an electronic indication of transaction validity associated with the second pending digital asset transaction;

(4) recording the electronic indication of transaction validity for the second pending digital asset transaction in the second tamper-evident log;

(x) accessing tamper-evident logs of at least some of the plurality of super peer computing nodes used to verify entries in the second tamper-evident log;

(xi) relaying to one or more gateway nodes the electronic indication of transaction validity for the second pending digital asset transaction to be delivered at least to respective user devices associated with the second pending digital asset transaction;

(xii) computing a respective independent instance of a second electronic ledger portion;

(xiii) receiving from the one of the others of the plurality of super peer computing nodes data comprising at least a minting second electronic ledger portion; and (xiv) comparing the respective independent instance of the second electronic ledger portion with the received data comprising at least the minting second electronic ledger portion, wherein the periodic schedule comprises a predefined frequency with which to append new electronic ledger portions to the first instance of the distributed electronic public ledger.

10. The system of claim 9, wherein the configuration software agent schedules computing roles for the plurality of super peer computing nodes according to a predefined schedule stored in respective non-transitory computer-readable memory operatively connected to the administrative super peer computing node and accessible by the configuration software agent.

11. The system of claim 9, wherein the configuration software agent schedules computing roles for the plurality of super peer computing nodes based at least in part upon any of respective available processing power of at least one of the plurality of super peer computing nodes, respective available transmission bandwidth of at least one of the plurality of super peer computing nodes, respective ownership or control of at least one of the plurality of super peer computing nodes, or geographic location of at least one of the plurality of super peer computing nodes.

12. The system of claim 9, wherein appending the first electronic ledger portion to the first instance of the distributed electronic public ledger comprises creation of a predefined amount of digital assets.

13. The system of claim 9, wherein the periodic schedule comprises one or more predefined times at which to append new electronic ledger portions to the first instance of the distributed electronic public ledger.

* * * * *